US010463263B2

(12) United States Patent
Alpert et al.

(10) Patent No.: US 10,463,263 B2
(45) Date of Patent: *Nov. 5, 2019

(54) MULTIPURPOSE HOST SYSTEM FOR INVASIVE CARDIOVASCULAR DIAGNOSTIC MEASUREMENT ACQUISITION AND DISPLAY

(71) Applicant: Volcano Corporation, San Diego, CA (US)

(72) Inventors: Howard David Alpert, El Dorado Hills, CA (US); Paul Michael Hoseit, El Dorado Hills, CA (US)

(73) Assignee: VOLCANO CORPORATION, San Diego, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 15/212,945

(22) Filed: Jul. 18, 2016

(65) Prior Publication Data
US 2016/0324426 A1    Nov. 10, 2016

Related U.S. Application Data

(60) Continuation of application No. 14/139,635, filed on Dec. 23, 2013, now Pat. No. 9,392,979, which is a continuation of application No. 11/555,556, filed on Nov. 1, 2006, now Pat. No. 8,636,659, which is a division of application No. 10/151,423, filed on May 20, 2002, now Pat. No. 7,134,994.

(51) Int. Cl.
| | | |
|---|---|---|
| *A61B 5/027* | (2006.01) | |
| *A61B 5/026* | (2006.01) | |
| *A61B 18/24* | (2006.01) | |
| *A61B 5/0215* | (2006.01) | |
| *A61B 5/00* | (2006.01) | |
| *A61B 8/06* | (2006.01) | |
| *A61B 8/12* | (2006.01) | |
| *A61B 5/01* | (2006.01) | |
| *A61B 5/0205* | (2006.01) | |
| *A61B 5/145* | (2006.01) | |
| *A61B 5/1473* | (2006.01) | |
| *A61B 8/00* | (2006.01) | |
| *A61B 8/08* | (2006.01) | |
| *G16H 40/63* | (2018.01) | |
| *G06F 19/00* | (2018.01) | |

(52) U.S. Cl.
CPC ............ *A61B 5/027* (2013.01); *A61B 5/0035* (2013.01); *A61B 5/0066* (2013.01); *A61B 5/0084* (2013.01); *A61B 5/01* (2013.01); *A61B 5/026* (2013.01); *A61B 5/0215* (2013.01); *A61B 5/02055* (2013.01); *A61B 5/1473* (2013.01); *A61B 5/14539* (2013.01); *A61B 5/6851* (2013.01); *A61B 5/6852* (2013.01); *A61B 5/72* (2013.01); *A61B 5/743* (2013.01); *A61B 5/7435* (2013.01); *A61B 5/7475* (2013.01); *A61B 8/06* (2013.01); *A61B 8/12* (2013.01); *A61B 8/468* (2013.01); *A61B 8/488* (2013.01); *G16H 40/63* (2018.01); *A61B 2560/045* (2013.01); *G06F 19/3418* (2013.01)

(58) Field of Classification Search
None
See application file for complete search history.

(56) References Cited

U.S. PATENT DOCUMENTS

| | | |
|---|---|---|
| 5,463,261 A | 10/1995 | Skarda et al. |
| 5,490,134 A | 6/1996 | Fernandes et al. |
| 5,549,109 A | 8/1996 | Samson |
| 5,724,985 A | 3/1998 | Snell et al. |
| 5,765,565 A | 6/1998 | Adair |
| 5,873,835 A | 2/1999 | Hastings et al. |
| 6,010,449 A | 1/2000 | Selmon |
| 6,078,747 A | 6/2000 | Jewitt |
| 6,083,170 A | 7/2000 | Ben-Haim |
| 6,148,095 A | 11/2000 | Prause et al. |
| 6,188,407 B1 | 2/2001 | Cruz et al. |
| 6,193,669 B1 | 2/2001 | Degany et al. |
| 6,221,012 B1 | 4/2001 | Maschke et al. |
| 6,322,502 B1 | 11/2001 | Schoenberg et al. |
| 6,361,497 B1 | 3/2002 | Lathbury et al. |
| 6,398,736 B1 | 6/2002 | Seward |
| 6,411,850 B1 * | 6/2002 | Kay .................. A61N 1/36521 607/19 |
| 6,450,964 B1 | 9/2002 | Webler |
| 6,471,656 B1 | 10/2002 | Shalman et al. |
| 6,615,071 B1 | 9/2003 | Casscells, III et al. |

(Continued)

FOREIGN PATENT DOCUMENTS

| | | |
|---|---|---|
| JP | 62122637 | 6/1987 |
| JP | 2000504249 | 4/2000 |

(Continued)

OTHER PUBLICATIONS

International Search Report for PCT/US06/40127 dated Apr. 5, 2007, 2 pages.
Written Opinion of the International Searching Authority for PCT/US06/40127 dated Apr. 5, 2007, 4 pages.
GE Marquette Medical Systems, Inc.; Section 2. 510(k) Summary of Safety and Effectiveness, Jun. 27, 2000, 5 pages.
Prucka CardioLab Electrophysiology Monitoring System, 2000, 2 pages.
U.S. Appl. No. 60/292,727, filed May 21, 2003.
Premarket Notification 510(k) Summary, Dec. 11, 2001,65 pages.
Cardiac Science, Quinton Q-Tel RMS, 2012, 5 pages.

(Continued)

Primary Examiner — Channing S Mahatan

(57) ABSTRACT

A multifunctional invasive cardiovascular diagnostic measurement host is disclosed that interfaces a variety of sensor devices, such as guide wire-mounted pressure sensors, flow sensors, temperature sensors, etc, and provides a multi-Mode graphical user interface providing a plurality of displays in accordance with the various types of sensors and measurements rendered by the sensors.

13 Claims, 20 Drawing Sheets

(56) References Cited

U.S. PATENT DOCUMENTS

| | | | |
|---|---|---|---|
| 6,673,015 | B1 | 1/2004 | Glover et al. |
| 6,754,608 | B2 | 6/2004 | Svanerudh |
| 6,788,967 | B2 | 9/2004 | Ben-Haim et al. |
| 6,813,512 | B2 | 11/2004 | Aldefeld et al. |
| 6,817,947 | B2 | 11/2004 | Tanskanen |
| 7,134,994 | B2 | 11/2006 | Alpert et al. |
| 10,130,310 | B2 * | 11/2018 | Alpert .................. A61B 5/7445 |
| 2002/0058861 | A1 | 5/2002 | Drew |
| 2002/0133239 | A1 | 9/2002 | Rebellius et al. |
| 2002/0198454 | A1 | 12/2002 | Seward et al. |
| 2003/0088291 | A1 * | 5/2003 | Anderson .......... A61N 1/37235 |
| | | | 607/32 |
| 2006/0165040 | A1 | 1/2006 | Rathod et al. |
| 2007/0016028 | A1 | 1/2007 | Donaldson et al. |
| 2007/0016029 | A1 | 1/2007 | Donaldson et al. |
| 2016/0073972 | A1 * | 3/2016 | Alpert .................. A61B 5/7445 |
| | | | 600/486 |

FOREIGN PATENT DOCUMENTS

| | | |
|---|---|---|
| JP | 2001100946 | 1/2001 |
| JP | 2001500749 | 1/2001 |
| JP | 2003116055 | 4/2003 |
| WO | WO 98129790 | 7/1998 |

OTHER PUBLICATIONS

Toshiba Debuts Nemio Ultrasound; Upgradeable System Partners High Performance with Flexibility and Affordability, May 8, 2001, 2 pages.
510(k) Summary of Safety arid Effectiveness: 21 CFR 807.92, Toshiba America Medical Systems, Mar. 15, 2001.
HP Announces Expanded Functionality, Breakthrough Technologies and New Name for Patient-Monitoring Family; New HP Viridia Patient Care System Encompasses Patient-side Testing, PC-based Central Workstations, Flexible Support and Financing, May 1, 1997, 4 pages.
Chapter 23: Summary of Safety and Effectiveness, Dec. 9, 1998, 5 pages.
Premarket Notification 510(k) Summary, Feb. 3, 2000, 5 pages.
Renaissance, Used Patient Monitors, www.mywebsiteguy.com, Jan. 20, 2012, 3 pages.
HP Viridia 24 patient monitor all there ready to go! www.ebay.com, Jan. 12, 2012, 5 pages.
Diagnostic Imaging: Acuson to shift Aegis miniPACS to Windows NT operating system, Jun. 1, 1997, 2 pages.
Diagnostic Imaging 3-D display: the big news for ultrasound products, 1996-2010, 4 pages.
Issue Stories; AIUM Celebrates the Technologies of Y2K, Medical Imaging, Mar. 2000, 3 pages.
Datex-Ohmeda S/5™ Network and Central, Viewing the whole picture wherever you are, 2001, 2 pages.
SmartFlow™ Integrated Lumen Physiology, Version 5.0, Operator's Manual, Apr. 2001.
Florence Medical Innovations in Vascular Technology Business Plan, May 2002.
Florence Medical SmartFlow, CFR/FFR Manual, Mar. 2002.
SmartFlow CFR/FFR, Innovations in Vascular Technology, Model 2000, 2002, 6 pages.
EPMedSystems, EP-WorkMate, Windows—for—WorkMate, User's Guide, 1996-2001.
EPMedSystems, EP-WorkMate, User's Guide, 1996-2000.
Florence Medical, Annual Letter to Shareholders, May 17, 2001, 1 page.
Florence Medical LTD, Company Profile, May 2001, 4 pages.
SmartFlow™ Integrated Lumen Physiology for the Cathlab, SmartFlow CFR/FFR, Model 2000, Version 5.0 CFR/FFR, 2001, 2 pages.
Florence Medical Center 510(k) Summary SmartFlow™, May 14, 2001, 6 pages.
Florence Medical Center 510(k) Summary SmartFlow™, Oct. 2, 2001, 5 pages.
Florence Medical, Inc. News Release, Florence Medical Introduces SmartFlow Multiple Lesion™ Device at American College of Cardiology Meeting, Mar. 14, 2002, 2 pages.
The Free Library by Farlex, Florence Medical Introduces SmartFlow Multiple Lesion Device at American College of Cardiology Meeting, Mar. 14, 2002, 3 pages.
Florence Medical innovations in vascular technology PowerPoint presentation, 2002.
GE Marquette Quotation to Chippenham-JW Hospitals, Richmond, VA, Jan. 23, 2001, 6 pages.
GE Medical Systems, Prucka CardioLab/Mac-Lab System Upgrade Installation Instructions, Software Version 5.0F, Dec. 19, 2000, 7 pages.
GE Medical Systems, CardioLab/Mac-Lab System, Software Only Client Installation: Instructions, Software Version 5.1D, Jun. 2002.
CardioLab II Plus Amplifier, Operator's Manual, Revision B, Jun. 15, 2000.
GE Medical Systems, Prucka CardioLab 2000/4000/7000, Operator's Manual, Software Version 5.1, Revision A, Aug. 9, 2001.
GE Medical Systems, Prucka CardioLab 2000/4000/7000, Operator's Manual, Software Version 5.1, Revision B, Aug. 1, 2001.
GE Medical Systems, Prucka CardioLab/Mac-Lab 7000, CardioLink Operator's Manual, Software Version 5.0G, Revision C, Jul. 2, 2001.
GE Medical Systems, CardioLab/Mac-Lab 2000/4000/7000, System Service Manual, Revision C, May 21, 2002.
Shalman, E., et al., Pergamon, Numerical modeling of the flow in stenosed coronary artery. The relationship between main hemodynamic parameters, Florence Medical, Received Nov. 3, 2000, accepted Oct. 2, 2001, 37 pages.
Shalman E., et al., Pergamon, Pressure-based simultaneous CFR and FFR measurements: understanding the physiology of a stenosed vessel, Received Jul. 18, 2000, accepted Oct. 6, 2000.
Grubert, Luis. M.D., et al., Simultaneous Assessment of Coronary Flow Reserve and Fractional How Reserve with a Novel Pressure-Based Method, Journal of Interventional Cardiology vol. 13, No. 5, 2000.
European Patent Office, "Communication—Extended European Search Report," for EP 12150922.8, dated May 18, 2012, 7 pages.
The Free Library by Farlex, EP MedSystems Reports Second Quarter and First Half Results; 30 Alert Systems Shipped Into Eurorean Market, Mount Arlington, NJ, Aug. 9, 2000, 5 pages.
EP-Workmate, The Completely Integrated EP WorkStation, EP MedSystems, Inc., Mount Arlington, NJ, 2001, 6 pages.
GE Medical Systems, Prucka Center for Invasive Cardiology, Sugar Land, TX, Product Information Bulletin, Apr. 26, 2001, 1 page.
Prucka Cardiolab 2000, Electrophysiology Diagnostic System, Prucka Center for Invasive Cardiology, GE Medical Systems Information Technologies, 8200 West Tower Avenue, Milwaukee, WI, 2000, 2 pages.
Prucka Cardiolab 4000, Electrophysiology Diagnostic System, Prucka Center for Invasive Cardiology, GE Medical Systems Information Technologies, 8200 West Tower Avenue, Milwaukee, WI, 2000, 2 pages.
Prucka Cardiolab 7000, Advanced Electrophysiology Diagnostic System, Prucka Center for Invasive Cardiology, GE Medical Systems Information Technologies, 8200 West Tower Avenue, Milwaukee, WI, 2000, 2 pages.
Business Library, EMPD to Introduce New Products Including Focal Recorder Catheter and EP-WorkMate With Windows at Naspe Conference; Also Filed for CE Approval of Alert-TD, CBS Interactive Business Network Resource Library, Mount Arlington, NJ, May 15, 2000, 2 pages.
National Instruments, Inc. Full Featured E Series Multifunction DAQ, downloaded Dec. 27, 2011; Product available sometime in 2001-2002, 11 pages.
Florence Medical SmartFlow Booth, Oct. 17, 2000, 2 pages.
United States District Court in and for the District of Delaware, Civil Action No. 10-631, *St. Jude Medical, Cardiology Division, Inc. et al.* vs. *Volcano Corporation*, Motion for Summary Judgment Hearing Transcript, Sep. 7, 2012, 166 pages.
U.S. Appl. No. 13/410,070, Third-Party Submission Under 37 CFR 1.290 Concise Description of Relevance, Feb. 14, 2013, 19 pages.

(56) References Cited

OTHER PUBLICATIONS

U.S. Appl. No. 13/410,070, Office Action dated Nov. 7, 2012, 17 pages.
U.S. Appl. No. 13/410,070, Amendment filed on Feb. 7, 2013 in response to Office Action dated Nov. 7, 2012, 18 pages.
U.S. Appl. No. 13/410,070, Interview Summary dated Feb. 26, 2013, 3 pages.
U.S. Appl. No. 13/410,099, Third-Party Submission Under CFR 1.290 Concise Description of Relevance, Feb. 27, 2013, 25 pages.
U.S. Appl. No. 13/410,099, Office Action dated Jan. 11, 2013, 27 pages.
U.S. Appl. No. 13/410,099, Amendment filed on Feb. 21, 2013 in response to Office Action dated Jan. 11, 2013, 17 pages.
U.S. Appl. No. 13/410,099, Interview Summary dated Feb. 26, 2013, 3 pages.
U.S. Appl. No. 60/292,727, filed May 23, 2002, 20 pages.
Petition for Inter Partes Review dated Apr. 30, 2013.
Mandatory Notices dated Apr. 30, 2013.
Moton Concerning Exhibits Not Filed by PRPS dated Apr. 30, 2013.
Motion to Seal Exhibits dated Apr. 30, 2013.
Power of Attorney dated Apr. 30, 2013.
List of Exhibits dated Apr. 30, 2013.
Notice of Filing Date Accorded to Petition dated May 6, 2013.
Decision to Make Non-Electronic Filing dated May 6, 2013.
Petition for Inter Partes Review dated May 8, 2013.
List of exhibits dated May 8, 2013.
Cover Letter with Notice of Filing Date dated May 8, 2013.
U.S. Pat. No. 7,134,994 ("The '994 patent").
Declaration of W. Anthony Mason ("Mason Decl."), Apr. 29, 2013.
Prucka CardioLab® 2000/4000/7000 Operator's Manual, Software Version 5.1 ("Prucka Manual")("Vadodaria IPR Decl., Ex. B") ("Prucka Decl., Ex. 9")., Aug. 9, 2001 (3 parts).
David A. Solomon, "Inside Windows NT Second Edition"; Microsoft Press, 1998 ("Inside Windows"). (3 parts).
U.S. Pat. No. 5,819,115 ("Hoese").
*St. Jude Medical, et al.* v. *Volcano Corporation*, Case No. 10-631-RGA (D. Del.), Complaint for Infringement., Sep. 20, 2010.
*Volcano Corporation* v. *St. Jude Medical, et al.*, Answer and Counterclaim of Infringement., Sep. 20, 2010.
*Volcano Corporation* v. *St. Jude Medical, et al.*, Responsive Pleading., Nov. 15, 2010.
*Volcano Corporation* v. *St. Jude Medical, et al.*, Counterclaim Dismissal., Oct. 22, 2012.
Federal Rule of Civil Procedure 3., Apr. 8, 2013.
Federal Rule of Civil Procedure 7., Apr. 8, 2013.
File History of U.S. Appl. No. 10/151,423., dated Feb. 28, 2011 (3 parts).
U.S. Appl. No. 10/151,423, Non-final rejection of Mar. 24, 2005.
U.S. Appl. No. 10/151,423, Amendment of Sep. 22, 2005.
U.S. Appl. No. 10/151,423, Non-final rejection of Feb. 14, 2006.
U.S. Appl. No. 10/151,423, Amendment of May 4, 2006.
MacMillan Dictionary of Information Technology, Third Edition, 1989, pp. 69, 105, and (MacMillan IT Dictionary).
Dale Rogerson ,"*Inside COM*", Microsoft's Component Object Model, Microsoft Press, WA, US, 1997, totaling 406 pages (4 Parts).
Elrad et al , "Aspect-Oriented Programming" Communications of the ACM, Oct. 2001, vol. 44, No. 10 ("Elrad, et al.").
Weiss et al., "Extending PCI Performance Beyond the Desktop", Computer vol. 32(6), Jun. 1999 ("Weiss, et al.").
*St. Jude Medical, et al.* v. *Volcano Corporation*, Case No. 10-631-RCA (D. Del.), Joint Claims Construction Brief filed Jul. 23, 2012 ("JCCB").
*St. Jude Medical, et al.* v. *Volcano Corporation*, Case No. 10-631-RCA (D. Del.), Amended Claim Construction Order of Oct. 12, 2012 ("CCO").
Ex parte Hackbarth, Appeal No. 2009-000934, 2010 Pat. App. Lexis 17699 (BPAI Dec. 1, 2010).
U.S. Pat. No. 6,193,669 ("the '669 patent") ("Barak Lit Decl., Ex. 3").

Krauss, et al., "LabView TM for sensor data acquisition", Trends in Analyt. Chem., vol. 18, No. 5, 1999 ("Kraus 1999").
Dictionary of Computing, 215 (4th ed. 1996).
SmartFlow™ Integrated Lumen Physiology, Version 5.0, Operator's Manual, Apr. 2001 ("Barak IPR Decl., Ex. P") ("Barak Lit Decl. Ex. 8").
IPR Declaration of Dr. Chen Barak ("Barak IPR Decl.")., Jan. 2, 2013.
Ex parte Mettke. Appeal 2006-0610, 2008 Pat. App. Lexis 6761, (BPAI Sep. 30, 2008).
Kern, et al., "From Research to Clinical Practice: Current Role of Intracoronary Physiologically Based Decision Making in the Cardiac Catheterization Laboratory", J. Am. Coll, Cardiol. 1997;30(3):613-620.("Kern 1997").
U.S. Pat. No. 5,873,835 ("Hastings").
U.S. Pat. No. 6,754,608 ("Svanerudh").
Svanerudth Provisional Application ("Svanerudh Prov.")., May 23, 2001.
U.S. Pat. No. 6,083,170 ("Ben-Haim").
U.S. Pat. No. 6,322,502 ("Schoenberg").
U.S. Pat. No. 5,724,985 ("Snell").
IPR Declaration of Sachin Vadodaria., Jan. 21, 2013.
*Stored Value Solutions* v. *Card Activation Services*, 796 F.Supp.2d 520 (D. Del. Jul. 1, 2011).
*Stored Value Solutions* v. *Card Activation Services*, 2012 WL 6097674 (2012).
*One Number Corp.* v. *Google, Inc.*, 2012 WL 3679746 (BPAI, Aug. 24, 2012).
Prucka CardioLab/Mac-Lab/ComboLab Preinstallation Manual, Aug. 2, 2001 ("Vadodaria IPR Decl., Ex., A").
Morris, "Object-Oriented Programming for Windows 95 and NT", Digital. Press (1999)("Morris") (4 parts).
CurriculumVitae of W. Anthony Mason, Apr. 30, 2013.
Peter G. Viscarota & W. Anthony Mason, "Windows NT Device Driver Development", New Riders (1999), p. 51.
Microsoft, MS Windows NT Kernel-mode User and GDI White Paper (2011) http://technet.microsoft.com/en-us/library/cc750820.aspx).
Daniel P. Bevel, Professor, University of Rome "Tor Vergata", Speech at the UnixForum Chicago (Mar. 8, 2001) (PowerPoint presentation available at www.uniforum.chi.il.us/slides/linuxkernel/LinuxKernel.ppt).
Search Storage, "What is a driver?" (Jun. 1997), http://searchstorage.techtarget.com/definition/driver.
PCI SIG, PCI Family History (2006) (available at http://www.pcisig.com/specifications/PCI_Family_History.pdf).
George T. Heineman & William T. Councill, Component-Based Software Engineering—Putting the Pieces Together, 6-14 (2001).
Microsoft Computer Dictionary p. 162, 5th ed. 2002.
McGraw-Hill Dictionary of Scientific and Technical Terms, pp. 1498 and 1643 (4th ed. 1989).
The Random House Dictionary of the English Language pp. 1542, 1579 and 1676 (2d ed. Unabridged 1987).
Declaration of Sheri Prucka (the "Prucka Decl.")., Dec. 13, 2011.
U.S. Pat. No. 5,463,261 to Skarda et al. ("Skarda").
The Birth of the IBM PC (available http://www-03.ibm.com/ibm/history/exhibits/pc25/pc25_birth.html, Jan. 12, 2012.
Life Pulse Fibre Channel Solutions—PCI Host Adapter Datasheet (1997).
"PCI Bus: Full-Speed Fibre Channel PCI Bus announced by Emulex Network Systems; LightPulse PCI host adapter Card Brings Gigabit Speeds to LAN and Storage at Half the Cost of Current Solutions", Edge: Work-Group Computing Report; Sep. 25, 1995 v6 n279 p. 21(1).
Declaration of Frank Martin (the "Martin Decl."), Nov. 18, 2011.
National Instruments Datasheet, "Full-Featured E Series Multifunction DAQ 12 or 16-Bit, up to 1.25 MS/s, up to 64 Analog Inputs"., Dec. 27, 2011.
Microsoft, Windows Dev. Center, LoadLibraryEx function http://msdn.microsoft.com/en-us/library/windows/desktop/ms684179%28v=vs.85%29.aspx, Apr. 17, 2013.
Declaration of Charles Bryan Byrd ("Byrd Decl.")., Jan. 20, 2012.

(56) References Cited

OTHER PUBLICATIONS

EP Medsysterns, Inc., Quarterly Report (Form 10-QSB), at 13 (Mar. 31, 2002) (available at http://www.sec.gov/Archives/edgar/date/1012394/000100547702002206/d0_2-37396.txt). [IPR Ex. 1068].
Open Systems Resources, Inc., "Read_Port_Ulong," htto://www.osronline.com/ddkx/kmarch/k103_3pki.htm (Apr. 11, 2003).
Microsoft Developer Network, "NdisMRegisterMiniport function," http://msdn.microsoft.com/en-us/library/windows/hardware/ff553602%28v=vs.85%29.aspx , Dec. 8, 2011.
Webster's New World Dictionary, 1162 (2d College Ed. 1984).
Rabiner, Lawrence et al., Theory and Application of Digital Signal Processing, Prentice-Hall, pp. 295-300 (1975).
National Instruments, Inc., Low-Cost E Series Multifunction DAQ—12 or 16-Bi, 200 kS/s, 16 Analog Inputs, (available at http://www.ni.com/pdf/products/us/4daqsc202-204_ETC_212 -213.pdf., , 2006.
GE Medical Systems, GE Medical Systems Information Technologies Introduces First and Only Networking Tool for CardioLab Electrophysiology Data (May 9, 2002).
See Microsoft, GE Healthcare Empowers Professionals with Windows Embedded-based Recording Systems Smart Design Helps Improve Workflow and Productivity (Feb. 17, 2011).
GE Medical Systems, New Tools Entrance Productivity and Accuracy in Electrophysiology Workflow and Diagnosis (May 8, 2001).
National Instruments. "NI PCI-6040E" http://sine.ni.com/nips/cds/print/p/lang/en/nid/10795. 2012.
Moore, Gordon, "Cramming more components onto integrated circuits," Electronics, vol. 38, No. 8 (Apr. 19, 1965).
U.S. Appl. No. 10/151,423, Notice of Allowability (dated Jul. 24, 2006).
CardioLab/Mac-Lab System Software Only Client Installation Instructions for Version 5.1D, Jun. 4, 2002 ("Vadodaria Lit Decl., Ex. D").
EuroPCR Brochure—SmartFlow™ Integrated Lumen Physiology, "Software Design Description" ("Barak IPR Decl., Ex. 4")("Barak Lit Decl., Ex. 4")., Apr. 30, 2013 (4 parts).
Prucka ComboLab Version 5,1 Installation Instructions, May 2, 2002 ("Vadodaria IPR Decl., Ex, C").
Biography of Sheri Prucka ("Prucka Decl., Ex. 1")., Apr. 30, 2013.
510(k) Summary for the Windows Versions of Prucka Mac-Lab and Prucka CardioLab, K001305, Apr. 2000 ("Prucka Decl., Ex. 2").
Specifications—Prucka CardioLab Series, Prucka CardioLab® Electrophysiology Monitoring System ("Prucka Decl., Ex. 3"). 2000.
Prucka CardioLabe 2000, Electrophysiology Diagnostic System. ("Prucka Decl., Ex. 4"). 2000.
Prucka CardioLab® 4000, Electrophysiology Diagnostic System. ("Prucka Decal., Ex. 5"). 2000.
Prucka CardioLab® 7000, Advanced Electrophysiology Diagnostic System. ("Prucka Decl., Ex. 6"). 2000.
CardioLabt®II Pius Amplifier Operator's Manual, Revision B, Nov. 15, 2000 ("Prucka Decl., Ex, 7").
CardioLabe®/Mac-Lab® 2000/4000/7000 System Service Manual, Revision C, ("Prucka Decl., Ex. 8")., May 21, 2002 (4 parts).
Prucka CardioLab/Mac-Lab System upgrade Installation Instructions for Version 5.0F, Dec. 19, 2000 ("Vadodaria Lit Decl., Ex. C").
Prucka Mao-Lab® 2000/4000/7000 Operators Manual, Software Version 5.1, Revision B ("Prucka Decl., Ex. 10")., Aug. 1, 2001 (3 parts).
Prucka CardioLab/Mac-Lab 7000, CardioLink Operator's Manual, Jul. 2, 2001 ("Prucka Decl., Ex. 11").
Product Information Bulletin sent by Terry Chang to Mac-Lab Classic Customers on Apr. 26, 2001("Prucka Decl., Ex. 12").
Biography of Frank Martin ("Martin Decl., Ex. 1")., Apr. 30, 2013.
Data sheet-Smartflow TM Integrated Lumen Physiology for the Cathlab, published by Florence Medical, 2001 ("Martin Decl.; Ex. 3").
Photographs (front and back), accurately depicting the Florence Medical booth with the SmartFlow at the Oct. 2000 TCT convention ("Martin Decl., Ex. 4") ("Barak Lit Decl., Ex. 9") ("Barak IPR Dect., Ex. 3").
Summary and 510(k) authorization K003122 issued by the FDA to Florence Medical on May 14, 2001("Martin Decl., Ex. 5") ("Barak Lit Decl., Ex. 10") ("Barak IPR Decl., Ex. 2").
Clinical Package sent by Florence Medical to Doctors in the United States starting in 2001 ("Martin Decl., Ex. 6").
Additional data sheets for the SmartFlow ("Martin Decl., Ex. 7")("Barak Lit Decl., Ex. 12")., 2002.
Photographs accurately Depicting One of Florence Medicals posters at Trade Shows ("Martin Decl., Ex. 8") ("Barak Lit Decl., Ex. 13")., Oct. 17, 2000.
Photograph of Florence Medicai's Booth at the EuroPCR Conference (with front and back) ("Martin Decl., Ex. 9") ("Barak Lit Deci., Ex. 14")., Oct. 17, 2000.
510(k) Premarket Notification K012947 for SmartFlow Multiple Lesion, dated Oct. 2, 2001("Martin Decl., Ex, 10") ("Barak Lit Decl., Ex. 15").
Press Release—Florence Medical introduces SmartFlow® Multiple Lesion Device at American College of Cardiology Meeting—issued by Florence Medical on Mar. 14, 2002. ("Martin Decl., Ex. 11").
Press Release—Florence Medical Introduces SmartFlow® Multiple Lesion Device at American College of Cardiology Meetina issued by Florence Medical on Mar. 14, 2002, ("Martin Decl., Ex. 12").
Annual Letter to Shareholders, dated May 17, 2001("Martin Decl., Ex. 16").
PowerPoint Presentation drafted by Frank Martin ("Martin Decl., Ex. 17"), 2002 .
Front Cover of a Manila Folder Maintained by Robert Stoddard, Former Chief Financial Officer of Florence Medical ("Martin Decl., Ex. 18") Apr. 30, 2013.
EP MedSystems Press Release—EPMO to introduce New Products Including Focal Recorder Catheter and EP-WorkMate With Windows at NASPE Conference; Also Filed for CE Approval of Alert-TD May 15, 2000 ("Byrd Dccl., Ex. B").
EP MedSystems Press Release—EP MedSysterns Reports Second Quarter and First Half Results: 30 Alert Systems Shipped Into European Market. (Aug. 9, 2000) ("Byrd Decl., Ex. C").
EP-WorkMate Brochure (2001) ("Byrd Decl., Ex. E").
EP-WorkMate User's Guide for EPWorkMate v. 2.11.5 (2000) ("Byrd Decl., Ex. F"), (3 parts).
EP-WorkMate Windows@-for-WorkMate User's Guide v.3.0.0 (2001) ("Byrd Decl., Ex. G"), (3 parts).
Litigation Declaration of Sachin Vadodaria ("Vadodaria Lit Decl. ")., Dec. 15, 2011.
Litigation Declaration of Dr. Chen Barak ("Barak Lit Decl.")., Dec. 4, 2011.
Biography of Dr. Chen Barak ("Barak Lit Decl., Ex. 1") Apr. 30, 2013.
SmartFlow Clinical Package ("Barak Lit Decl., Ex. 11")., Apr. 30, 2013.
SniartFlow® CFR/FFR Manual ("Barak Lit Decl., Ex. 18")., Apr. 30, 2013.
Declaration of Matthew A. Smith., Apr. 30, 2013.
Default Protective Order of Appendix B of Trial Practice Guide, Apr. 30, 2013.
GE Medical Systems Information Technologies Introduces First and Only Networking Tool, May 9, 2002, 2 pages.
National instruments, PCI-6040E, 2011, 6 pages.
Webster's New World Dictionary, 1980, 3 pages.
National Instruments LabVIEW User Manual, Jul. 2000, 272 pages.
LabView Data Acquisition Basics Manual, Jul. 1999, 331 pages.
National Instruments, Inc Full-Featured E Series Multifunction DAQ, 2006, 11 pages.
Read_Port_Ulong, Apr. 11, 2003, 1 page.
NdisMRegisterMiniport function, Dec. 8, 2011, 7 pages.
EP-MedSystems From 10-QSB for the quarterly period ended Mar. 31, 2002, 19 pages.
Svanerudh, Johan, et al., U.S. Appl. No. 60/292,727, May 23, 2001, 30 pages.
Eriksson, Eva, Declaration, Nov. 14, 2011, 25 pages.
Ehrenberg, Heather L., Declaration, Nov. 17, 2011, 3 pages.
EuroPCR Booklet, May 22, 2001, 19 pages.
EuroPCR Newsletter, May 22, 2001, 16 pages.

(56) References Cited

OTHER PUBLICATIONS

Alpert, Howard David, et al., File History of U.S. Appl. No. 10/151,423, dated May 20, 2002 through Sep. 3, 2010, 216 pages.
Quinton,—510(k) Summary, Jan. 25, 2001, 5 pages.
Toshiba Debuts Nemio Ultrasound; Upgradeable System Partners High Performance, May 8, 2001, 2 pages.
Florence Medical SmartFlow Booth, 2000, 2 pages.
Real Time Mapping of Interventional Pressure Changes During Interventional Procedures Board and Determination of the Coronary Status Board, Oct. 18, 2000, 2 pages.
Florence Medical Booth, 2000, 1 page.
Bidgood, W. Dean, Understanding and Using DICOM, the Data Interchange Standard for Biomedical Imaging, Journal of the American Medical Informatics Association, vol. 4, No. 3, May / Jun. 1997.
USPTO, Final Office Action issued for U.S. Appl. No. 11/555,556 dated Jul. 30, 2012, 22 pages.
USPTO, Office Action issued for U.S. Appl. No. 11/555,556 dated Dec. 10, 2012, 20 pages.
USPTO, Office Action issued for U.S. Appl. No. 13/41,099 dated Oct. 24, 2012.
USPTO, Office Action issued for U.S. Appl. No. 13/410,070 dated Nov. 7, 2012.
Redacted Version of Volcano Corporation's Opening Brief in Support of its Motions for Summary Judgment, filed Jul. 13, 2012, 47 pages.
Redacted Version of St. Jude's Opening Brief in Support of its Motions for Summary Judgment, filed Jul. 13, 2012, 47 pages.
Redacted Version of Volcano Corporation's Opposition to St. Jude's Opening Brief in Support of its Motion for Summary Judgment, filed Aug. 10, 2012, 46 pages.
Redacted Version of St. Jude's Answering Brief in Opposition to Volcano's Seventeen Motions for Summary Judgment, filed Aug. 10, 2012, 44 pages.
Redacted Version of Volcano Corporation's Reply Brief in Support of its Motion far Summary Judgment, filed Aug. 20, 2012, 27 pages.
Redacted Version of St. Jude's Brief in Support of its Motions for Summary Judgment, filed Aug. 20, 2012, 25 pages.
Redacted Version of St. Jude Medical, et al. v. Volcano Corporation, '994 Patent invalidity, Infringement, Construction, Ex F—Part 1, Filed Oct. 3, 2012, 17 pages.
Redacted Version of St. Jude Medical, et al. v. Volcano Corporation, '994 Patent Invalidity, Infringement, Construction, Ex F—Part 2, Filed Oct. 3, 2012, 17 pages.
Redacted Version of St. Jude Medical, et al. v. Volcano Corporation, '994 Patent Invalidity, Infringement, Construction, Ex F—Part 3, Filed Oct. 3, 2012, 18 pages.
Redacted Version of St. Jude Medical, et al. v. Volcano Corporation, '994 Patent Invalidity, Infringement, Construction, Ex F—Part 4, Filed Oct. 3, 2012, 16 pages.
Redacted Version of St. Jude Medical, et al. v. Volcano Corporetion, '994 Patent Invalidity, Infringement, Construction, Ex F—Part 5, Filed Oct. 3, 2012, 16 pages.
Redacted Version of St. Jude Medical, et al. v. Volcano Corporation, '994 Patent Invalidity, Infringement, Construction, Ex F—Part 6, Filed Oct. 3, 2012, 11 pages.
C.A. No. 1:10-631-SLR, *St. Jude Medical* v. *Volcano Corporation*, Opening Brief in Support of Plaintiffs' Motion to Amend Complaint, Answer; and Counterclaims to Volcano's Second Amended Answer to Complaint for Patent Infringement and Counterclaims, Redacted Public Version, Oct. 31, 2011, 22 pages.
C.A. No. 1:10-cv-00631-SLR, *St. Jude Medical* v. *Volcano Corporation*, Volcano Corporation's Answering Brief in Opposition to Plaintiffs' Motion to Amend Complaint, Answer, and Counterclaims to Volcano's Second Amended Answer to Complaint for Patent Infringement and Counterclaims, Redacted, Nov. 11, 2011, 25 pages.
C.A. No. 1:10-631-SLR, *St. Jude Medical* v. *Volcano Corporation*, Reply Brief in Support of Plaintiffs' Motion to Amend Complaint, Answer, and Counterclaims to Volcano's Second Amended Answer to Complaint for Patent Infringement and Counterclaims, Redacted Public Version, Dec. 15, 2011; 16 pages.
C.A. No. 1:10-631-RGA, *St. Jude Medical* v. *Volcano Corporation*, First Amended Complaint for Patent Infringement, Jury Trial Demanded—Redacted Version, Apr. 27, 2012, 81 pages.
C.A. No. 1:10-631-RGA, *St. Jude Medical* v. *Volcano Corporation*, Plaintiffs' Joint Amended Answer to Defendant Volcano Corporation's Second Amended Answer to Complaint for Patent Infringement and Counterclaim, Jury Trial Demanded—Redacted Version, Apr. 27, 2012, 59 pages.
C.A. No. 1:10-631-RGA-MPT, *St. Jude Medical* vs. *Volcano Corporation*, Volcano Corporation's Brief in Opposition to Plaintiffs' Motion to Strike the Expert Report of Volcano's "Patent Law Expert" and Cross-Motion to Strike Expert Reports of St. Jude's Inequitable Conduct Experts, Jury Trial Demanded—Punlic Version, May 18, 2012, 27 pages.
C.A. No. 1:10-631-RGA, *St. Jude Medical* v. *Volcano Corporation*, Plaintiffs' Response Brief in Opposition to Volcano's Motion to Strike the Expert Reports of W. Anthony Mason and Dr. Khali Najafi, Redacted Public Version, Jun. 4, 2012, 26 pages.
C.A. No. 1:10-631-RGA-MPT, *St. Jude Medical* v. *Volcano Corporation*, Exhibits 1-9, Redacted, Jun. 4, 2012, 84 pages.
C.A. No. 1:10-631-RGA-MPT, *St. Jude Medical* v. *Volcano Corporation*, Exhibit 10, Part 1, Redacted, Jun. 4, 2012, 11 pages.
C.A. No. 1:10-631-RGA-MPT, *St. Jude Medical* v. *Volcano Corporation*, Exhibit 10, Part 2, Redacted, Jun. 4, 2012, 11 pages.
C.A. No. 1:10-631-RGA-MPT, *St. Jude Medical* v. *Volcano Corporation*, Exhibit 10, Part 3, Redacted, Jun. 4, 2012, 12 pages.
C.A. No. 1:10-631-RGA-MPT, *St. Jude Medical* v. *Volcano Corporation*, Exhibits 11-14, Redacted, Jun. 4, 2012, 18 pages.
C.A. No. 1:10-631-RGA-MPT, *St. Jude Medical* v. *Volcano Corporation*, Exhibits 15-33, Redacted, Jun. 4, 2012, 78 pages.
C.A. No. 1:10-631-RGA-MPT, *St. Jude Medical* v. *Volcano Corporation*, Volcano Corp.'s Reply Brief in Support of its Cross-Motion to Strike Expert Reports of St. Jude's Inequitable Conduct Experts, Redacted Version, Jun. 11, 2012, 14 pages.
European Patent Office, European Search Report for EP 12112643.4, dated Aug. 3, 2013, 8 pages.
European Patent Office, European Search Report for EP 12172646.7, dated Aug. 3, 2013, 8 pages.
Oxford University Press, Dictionary of Computing, 1997, 3 pages.
Microsoft Microsoft Computer Dictionary, Fifth Edition, 2002, 12 pages.
Computer Dictionary, Fourth Edition, 1999, 3 pages.
McGraw Hill Dictionary of Scientific and Technical Terms, Fourth Edition, 2006, 5 pages.
Loadlibrary Function, Nov. 15, 2011, 10 pages.
Motorola Addendum to M68000 User Manual, Aug. 7, 1997, 26 pages.
European Patent Office, "Examination Report" for Application No. 12 172 646.7, dated Jan. 28, 2015, 4 pages.

\* cited by examiner

| PATIENT/SYSTEM INFORMATION DISPLAY REGION |

HIERARCHICAL MENU DISPLAY REGION
304

306

| System | Pressure | Flow | Combo |

| SYSTEM MESSAGE DISPLAY REGION |

302

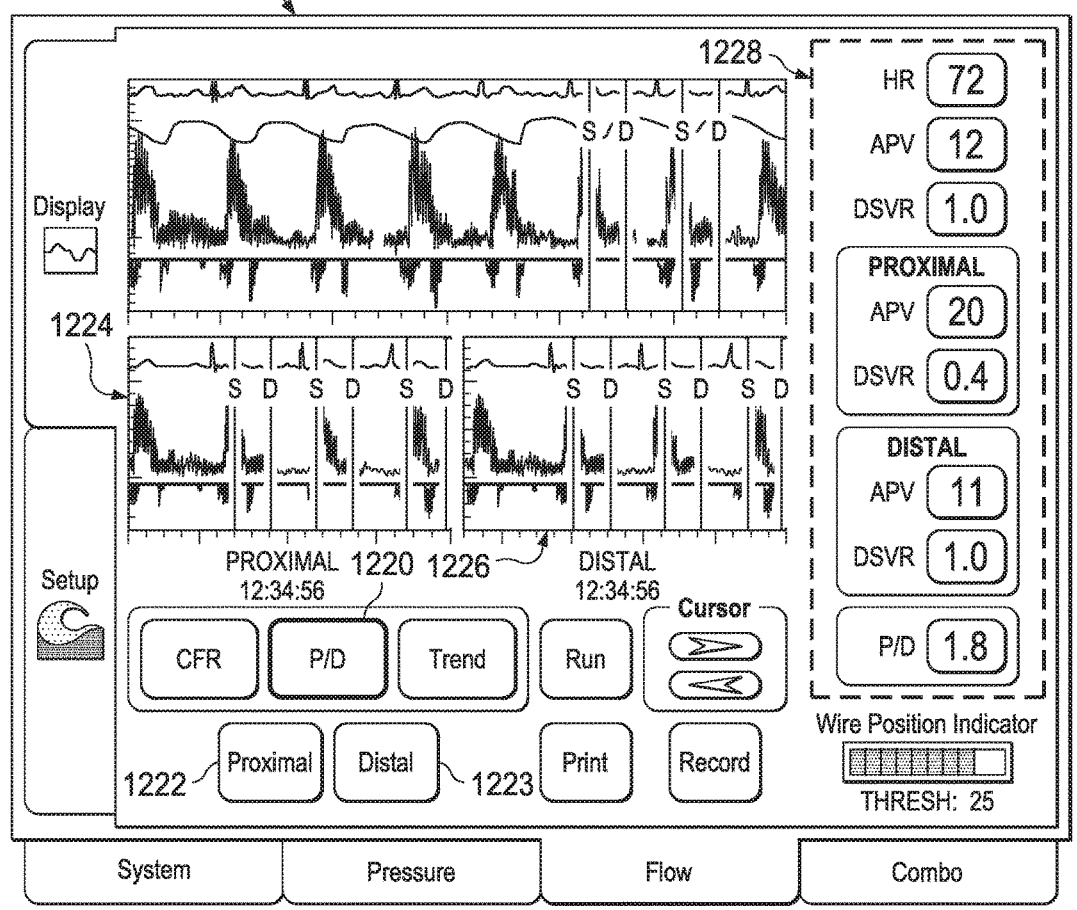

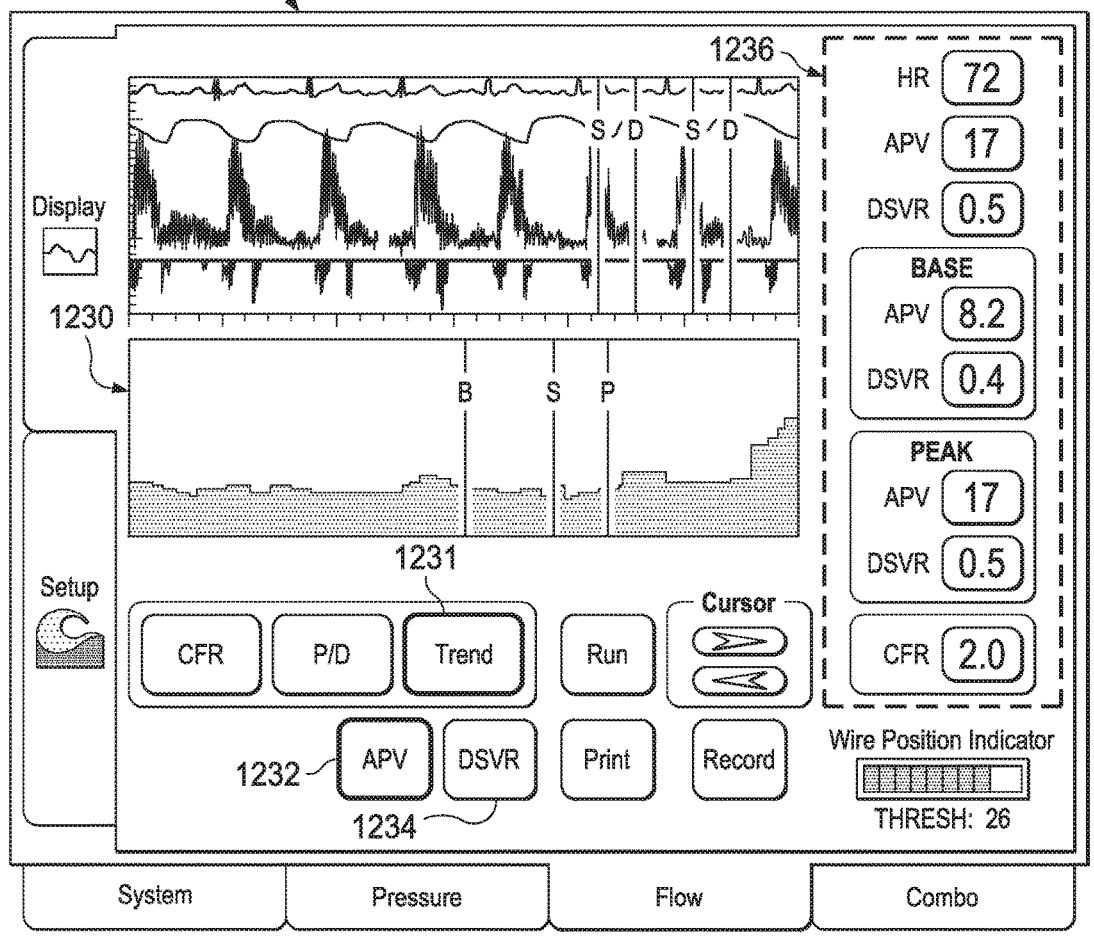

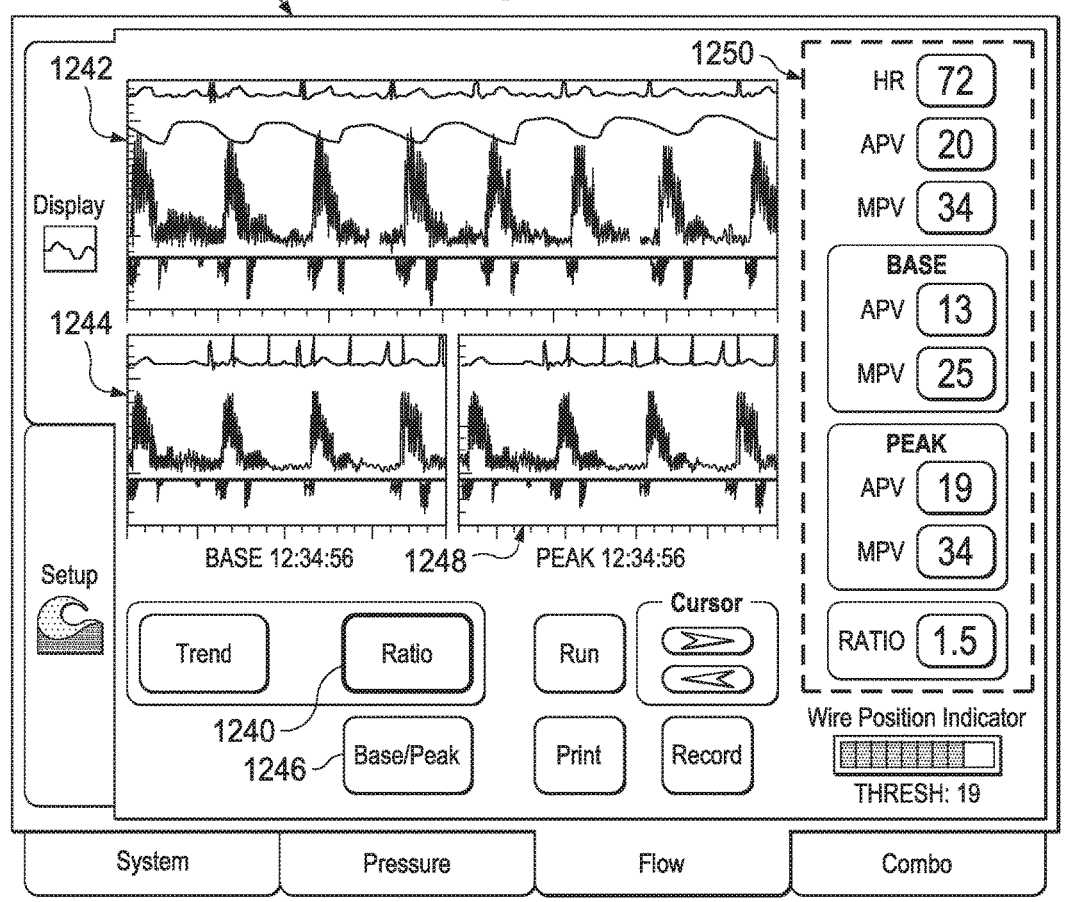

MULTIPURPOSE HOST SYSTEM FOR INVASIVE CARDIOVASCULAR DIAGNOSTIC MEASUREMENT ACQUISITION AND DISPLAY

CROSS-REFERENCE TO RELATED APPLICATIONS

This application is a continuation of U.S. patent application Ser. No. 14/139,635, filed Dec. 23, 2013, now U.S. Pat. No. 9,392,979, which is a continuation of U.S. patent application Ser. No. 11/555,556 filed on Nov. 1, 2006, now U.S. Pat. No. 8,636,659, which is a divisional of U.S. patent application Ser. No. 10/151,423 filed on May 20, 2002, now U.S. Pat. No. 7,134,994, each of which is hereby incorporated by reference in its entirety.

AREA OF THE INVENTION

The present invention generally relates to the area of diagnostic medical equipment, and more particularly to diagnostic devices for identifying and/or verifying efficacy of treatment of problematic blockages within coronary arteries by means of sensors mounted upon the end of a flexible elongate member such as a guide wire.

BACKGROUND OF THE INVENTION

Innovations in diagnosing and verifying the level of success of treatment of cardiovascular disease have migrated from external imaging processes to internal, catheterization-based, diagnostic processes. Diagnosis of cardiovascular disease has been performed through angiogram imaging wherein a radiopaque dye is injected into a vasculature and a live x-ray image is taken of the portions of the cardiovascular system of interest. Magnetic resonance imaging (MRI) has also been utilized to non-invasively detect cardiovascular disease. Diagnostic equipment and processes also have been developed for diagnosing vasculature blockages and other vasculature disease by means of ultra-miniature sensors placed upon a distal end of a flexible elongate member such as a catheter, or a guide wire used for catheterization procedures.

One such ultra-miniature sensor device is a pressure sensor mounted upon the distal end of a guide wire. An example of such a pressure sensor is provided in Corl et al. U.S. Pat. No. 6,106,476, the teachings of which are expressly incorporated herein by reference in their entirety. Such intravascular pressure sensor measures blood pressure at various points within the vasculature to facilitate locating and determining the severity of stenoses or other disruptors of blood flow within the vessels of the human body. Such devices are presently used to determine the need to perform an angioplasty procedure by measuring blood pressure within a vessel at multiple locations, including both upstream and downstream of a stenosis and measuring a pressure difference that indicates the severity of a partial blockage of the vessel.

In particular, a guide wire mounted pressure sensor is utilized to calculate fractional flow reserve (or "FFR"). In the coronary arteries, FFR is the maximum Myocardial flow in the presence of stenosis divided by the normal maximum myocardial flow. This ratio is approximately equal to the mean hyperemic (i.e., dilated vessel) distal coronary pressure Pd divided by the mean arterial pressure Pa. Pd is measured with a pressure sensor mounted upon a distal portion of guide wire or other flexible elongate member after administering a hyperemic agent into the blood vessel causing it to dilate. Pa is measured using a variety of techniques in areas proximal of the stenosis, for example, in the aorta.

FFR provides a convenient, cost-effective way to assess the severity of coronary and peripheral lesions, especially intermediate lesions. FFR provides an index of stenosis severity that allows rapid determination of whether an arterial blockage is significant enough to limit blood flow within the artery, thereby requiring treatment. The normal value of FFR is about 1.0. Values less than about 0.75 are deemed significant and require treatment. Treatment options include angioplasty and stenting.

Another such known ultra-miniature sensor device is a Doppler blood flow velocity sensor mounted upon the end of a guide wire. Such device emits ultrasonic waves along the axis of a blood vessel and observes a Doppler-shift in reflected echo waves to determine an approximation of instantaneous blood flow velocity. A Doppler transducer is shown in Corl et al. U.S. Pat. No. 6,106,476 on a guide wire that also carries a pressure transducer. Such devices are presently used to determine the success of a treatment to lessen the severity of a vessel blockage.

In particular, a Doppler transducer sensor is utilized to measure Coronary Flow Reserve (or "CFR"). CFR is a measure for determining whether a stenosis is functionally significant after treatment (e.g., post-angioplasty). CFR comprises a ratio of the hyperemic average peak velocity of blood flow to the baseline (resting) average peak velocity. Instantaneous peak velocity (IPV) is the peak observed velocity for an instantaneous Doppler spectrum provided by a Doppler transducer. An exemplary method of calculating an average peak velocity (APV) comprises averaging a set of IPV's over a cardiac cycle.

A known technique for determining whether an angioplasty was effective was to perform angioplasty, wait a few days, then perform thalium scintigraphy (imaging). If the angioplasty procedure was not effective, then re-intervention was performed and the lesion was again treated via angioplasty. On the other hand, using CFR, a flow measurement is taken immediately after angioplasty or stenting. The flow measurement is utilized to determine whether adequate flow has been restored to the vessel. If not, the balloon is inflated without the need for secondary re-intervention. A normal CFR is greater than about 2 and indicates that a lesion is not significant. Lower values may require additional intervention. In addition to being used post-treatment to determine the efficacy of treatment, CFR may be measured prior to treatment to determine if treatment is required.

A guide wire combination device, comprising a pressure sensor and a flow sensor having substantially different operational characteristics, was disclosed in the Corl et al. U.S. Pat. No. 6,106,476. While it has been proposed within the Corl et al. U.S. Pat. No. 6,106,476 to combine pressure and flow sensors on a single flexible elongate member, the prior art does not address how such a combination sensor is coupled to consoles that display an output corresponding to the signals provided by the flexible elongate member corresponding to the sensed pressure and flow within a vessel. Indeed, the relevant art comprises special-purpose monitors having static display interfaces that display a static set of parameters corresponding to a particular fixed set of diagnostic measurements (e.g., an aortic pressure and a pressure taken from a location proximate a stenosis). Thus, one type of monitor is utilized to process and display sensed pressure within a blood vessel. Another type of monitor provides output relating to blood flow within a vessel. As new intravascular diagnostic devices are developed, yet other special-purpose monitors/consoles are developed to display to a physician the sensed parameters.

There is substantial interest in simplifying every aspect of the operating room to reduce the incidence of errors. As one can imagine, the aforementioned intravascular pressure sensors are utilized in operating room environments including many types of sensors and equipment for diagnosing and treating cardiovascular disease. Clearly, the room for error is very limited when performing such activities. Notwithstanding the interest to keep equipment and operations simple, there exists a variety of different sensors that are potentially inserted within a human vasculature to diagnose arterial disease (e.g., blockages) and/or monitor vital signs during a medical procedure. The approach taken in the field of interventional cardiac imaging has been to provide multiple, special-purpose monitor consoles. Each monitor type is linked to a particular type of sensor device.

In a known prior intravascular pressure sensor-to-physiological monitor interface arrangement, marketed by JOMED Inc. of Rancho Cordova, Calif., a physiology monitor receives and displays, on a permanently configured display interface, a set of pressure values corresponding to two distinct pressure signals that are received by the monitor. A first pressure signal is provided by an aortic pressure sensor, and a second pressure signal corresponds to a pressure sensed by a distally mounted solid-state pressure sensor mounted upon a guide wire. The display interface of the monitor is permanently configured to output parameter values corresponding to those two signals. Thus, if display of for example, a flow signal value is desired, then a separate monitor, such as JOMED Inc.'s FloMap, is used.

SUMMARY OF THE INVENTION

The present invention provides addresses a need to provide a flexible, multipurpose host system for processing and displaying signals rendered by invasive cardiovascular sensors to reduce the amount of equipment and complexity of procedures for diagnosing and determining the efficacy of treatment of cardiovascular stenoses.

In particular, the present invention comprises a multipurpose host system that facilitates invasive cardiovascular diagnostic measurement acquisition and display. The host system includes a number of modularized components. The host system includes an external input signal bus interface for receiving data arising from cardiovascular diagnostic measurement sensors such as, for example, pressure transducers, Doppler flow transducers, temperature sensors, pH sensors, optical sensors, etc.

The host system also includes a plurality of measurement processing components for receiving data of particular sensor types. The processing components render diagnostic measurement parameter values according to the received data arising from various types of attached sensors. In a particular embodiment, the processing components are instantiated at startup time from component modules that are dynamically integrated into the host system. This allows the functionality of the host system to be extended to include new types of sensors without requiring an overhaul of the existing system software.

The host system also includes a multi-mode graphical user interface host. The interface host comprises a set of diagnostic measurement user interfaces. The output interfaces are integrated with the processing components and carry out displaying, on a graphical user interface a set of output values corresponding to parameter values rendered by the processing components.

BRIEF DESCRIPTION OF THE DRAWINGS

While the appended claims set forth the features of the present invention with particularity, the invention, together with its objects and advantages, may be best understood from the following detailed description taken in conjunction with the accompanying drawings of which:

FIG. 3 depicts an exemplary generic graphical user interface specification upon which a set of graphical displays are based in accordance with the various graphical user interface modes supported by a host system embodying the present invention;

FIGS. 12a-e depict an exemplary graphical user interface for a display sub-screen of a flow display mode of the host system;

DETAILED DESCRIPTION OF THE DRAWINGS

A multipurpose host system for invasive cardiovascular diagnostic measurement acquisition and display provides an advantage of the prior known systems in regard to its ability to present multiple user display interfaces. Each of the display interfaces corresponds to a particular purpose for which the multipurpose host is currently configured based, for example, upon one or more sensor devices communicatively coupled to its external signal interface. The host system is used, for example, in conjunction with interventional cardiology, e.g., angiography, or interventional procedures, e.g., angioplasty, to evaluate the hemodynamic status of an arterial blockage.

Figure 1:
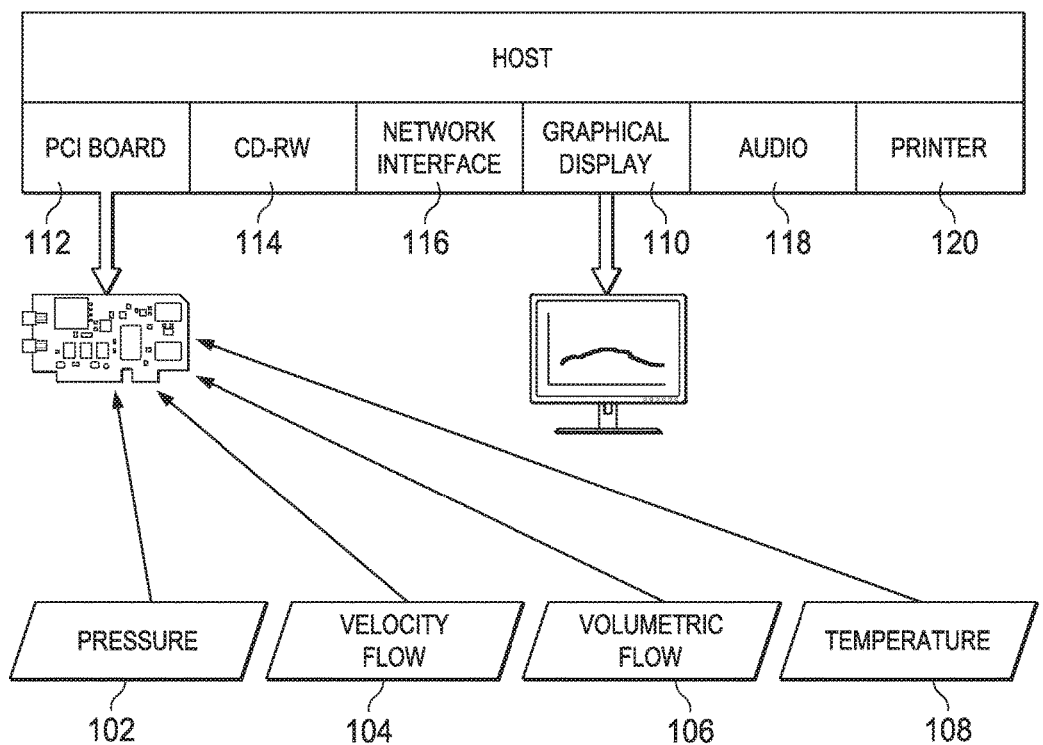
FIG. 1 is a schematic drawing depicting a system for conducting invasive cardiovascular diagnoses including an external input signal interface for receiving diagnostic parameter values of multiple types and a multimode graphical user interface for presenting the values according to a user-selected one of the multiple display modes.

With reference to FIG. 1, a multipurpose host system 100 is, by way of example, a personal computer architecture-based system for assessing real-time invasive cardiovascular parameters from within a blood vessel (e.g., blood pressure and flow measurements). The multipurpose host processes input signals from Multiple micro-miniature guide wire-mounted sensors (e.g., Doppler and pressure transducers) to produce real-time measurements, display various waveforms and derived parameters, and output high-level voltages proportional to calculated parameter values. The devices that supply the various data input signals are represented by pressure input 102, velocity flow input 104, volume flow 106, and temperature input 108. In an embodiment of the invention, the devices that provide the input to the host system 110 are presently used in existing, special-purpose processing boxes. This set is exemplary, as those skilled in the art will readily appreciate in view of this disclosure that alternative systems advantageously receive and process such diagnostic inputs as pH, ultrasound and light-based cross-sectional images of a vessel, biochemical markers, light spectrometry for tissue characterization, etc. It is further noted that the displayed output of the host system 100 is not limited to producing the measured parameters. Rather, the various modes of the host system 100 are capable of synthesizing generalized measures of physiological status (e.g., whether a blockage is severe and needs treatment) based upon the input parameter values.

The host system 100 operates in a plurality of modes, and each mode includes its own distinct graphical interface (rendered on graphical output display 110) and input parameter values (provided via a peripheral component interconnect (PCI) card 112) corresponding to particular sensor types. The PCI card 112 includes, by way of example, a digital signal processor (DSP) that samples data provided by the communicatively coupled input sensors and processes the sampled data to render digital data in a format expected by higher level components of the host system 100. Exemplary processes performed by the DSP include: A/D and D/A conversions, FFTs, level shifting, normalizing, and scaling. After processing the data, it is stored in a dual port RAM accessed, via the PCI bus of the host 100, by higher level application processes executing on the host system 100.

In the exemplary embodiment, input sensor types driving the output displays include pressure, flow, and temperature sensors mounted upon a flexible elongate member including combinations thereof placed, for example, upon a single guide wire or catheter. In fact, the flexible module-based architecture (see, FIG. 2) of the exemplary host system 110, which supports simultaneous display of multiple distinct types of input signals on a single graphical user interface, is particularly well suited for such combination devices since their output can be simultaneously monitored on a single interface even though modules that process the sensor inputs execute independently within the host system 100.

The exemplary host system 100 operates in pressure, flow, and combination (pressure/flow) modes. Though not essential to the invention, operation of each mode is preferably independent of the other modes, and each diagnostic display mode is driven by a designated set of parameter generation modules associated with particular input signals received by the host system from a communicatively coupled sensor. The pressure mode provides the user with a selection of calculated/derived parameters such as for example: proximal-distal pressure gradient, distal/proximal pressure ratio, normalized pressure ratio, and fractional flow reserve (normalized pressure ratio under hyperemic conditions). In an exemplary embodiment, the flow mode is divided into three operational modes: peripheral, coronary, and research. The peripheral mode acquires measurements in the cerebral or peripheral vasculature. The coronary mode acquires measurements in the coronary arteries. The research mode provides a superset of peripheral and coronary modes plus additional parameters that may be of interest in a clinical research environment. The combination mode allows parameters associated with pressure and flow modes to be displayed simultaneously on a single graphical display.

In the illustrative embodiment of the invention, the graphical display interface 110 depicts calculated pressure and flow information on a strip chart graph on a graphical user interface display. The current values are, for example, displayed numerically as well. The graph scrolls as new information is calculated and added. A graphically displayed control enables a user to freeze the scrolling graphs and scroll backwards to view previously displayed portions of the scrolling graph. Additional display methods and techniques will be apparent to those skilled in the art.

The host system 100 embodies an extensible, component-based architecture, and thus the host system 100 supports a virtually limitless number of operating modes for processing and rendering graphical display output corresponding to an extensible set of input signals provided by sensors measuring a variety of types and combinations thereof. The host system 100 is modularized to support receiving and processing signals in a variety of formats from a variety of instruments. In a particular exemplary embodiment of the invention, the host system 100 relies on transducers and external diagnostic instrumentation to: (1) process the raw sensor information rendered by transducers/sensors inserted within a patient and (2) provide the information to the host 100 in particular digital or analog formats. The host system 100's capabilities are extendable, by way of example through enhancements to a currently installed peripheral component interconnect (PCI) board 110 or the addition of new PCI boards, to include additional signal processing capabilities. In an exemplary embodiment, transducers on the guide wire (patient isolated) provide low-level signals for blood velocity, flow, and pressure. A standard external pressure transducer (patient isolated) may be integrated with the host system to provide low-level aortic pressure. A high-level ECG signal input to the host provides synchronization for calculations (not patient isolated).

The interface of the host system 100 comprises a number of additional interfaces supporting the transfer and storage of information relating to the operation of the host system. Data storage device 114, for example, a CD-RW or a DVD-RW drive, is utilized to upload new software and store patient data processed and displayed during a diagnostic/treatment procedure. A network interface 116 provides remote access for performing functions similar to those provided by the data storage device 114. An audio input 118 enables annotation of input records by a user. A printer 120 facilitates printing out labels and/or compiled data from a diagnostic/treatment procedure. The set of peripheral/interface components identified in FIG. 1 is exemplary. As those skilled in the art will readily appreciate there exist a vast variety of I/O devices that can be advantageously incorporated into the host system 100 to enhance its utility.

Figure 2:
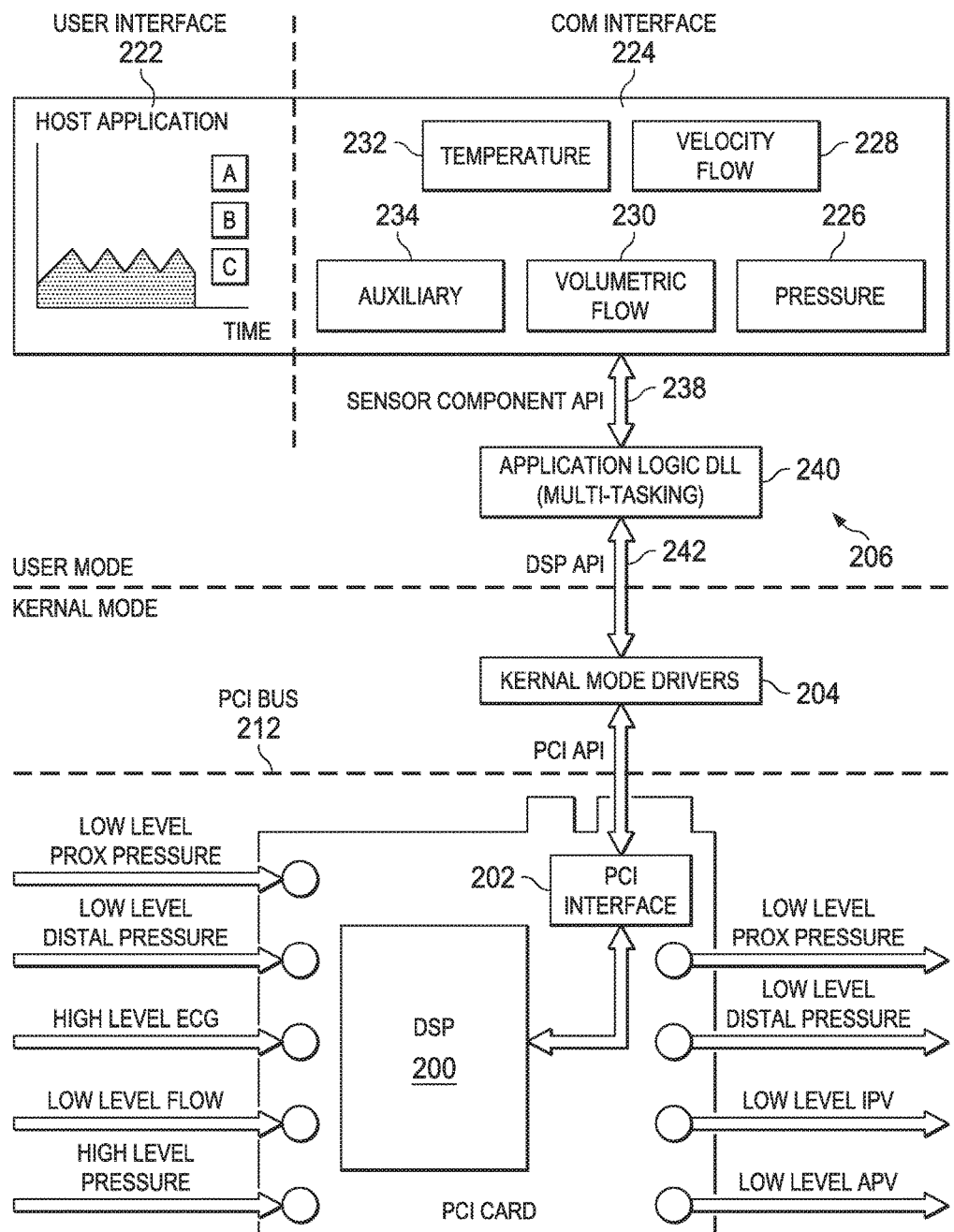
FIG. 2 is a schematic drawing depicting an exemplary architecture of the system depicted in FIG. 1.

Having described the peripheral components and external interfaces of an exemplary host system 100, attention is now directed to FIG. 2 that depicts an exemplary internal, architecture of the host system 100 that facilitates operation of the host 100 in a variety of display modes associated with a variety of sensed invasive cardiovascular parameters such as temperature, pressure and blood flow within an artery. The PCI card 112 represents a highly flexible component of the host system 100 architecture. The PCI card 112 includes a set of external sensor interface circuits for transmitting power and excitation signals to sensor devices and receiving sensed parameter values illustratively depicted in FIG. 2. In the illustrative example, the PCI card 112 includes both analog and digital input and output signals. Analog output signals are driven by the PCI card 112 output circuitry according to control commands supplied by high level user mode processes executing on the host system 100.

It is noted that a wide variety of sensor types are known and the host system 100 is not limited to any particular type of sensor input. To the contrary, the present host system 100 is intended to provide a broad, extensible, multipurpose platform upon which a wide variety of application-specific modules are capable of processing and displaying sensor data rendered by a variety of sensor types and combinations of the sensor types including those described, by way of example herein.

The PCI card 112 includes a digital signal processor (or DSP) 200 that operates as a special purpose co-processor on the host system 100. The DSP 200 receives digital samples corresponding to signals received via external inputs to the PCI card 112, and carries out appropriate processing (e.g., FFT, filtering, scaling, normalizing, etc.) on the digital/digitized data samples. Thereafter, the processed data is placed into a dual port RAM within the PCI bus interface 202.

Kernel mode drivers 204 executing on the host 100 facilitate communicating commands and data between the PCI card 112 and a set of user mode processes 206 that drive input parameter values for the multiple graphical user interface modes supported by the host system 100. The kernel mode drivers 204 communicate with the PCI bus interface 202 according to a set of methods defined by a PCI Application Program. Interface (API) 212. The kernel mode drivers 204 access PCI registers and ports on the PCI bus interface 202 to extract processed sensor data and to issue control commands to the PCI card 112. The kernel mode driver 204 carries out other desired driver functionality including issuing startup and diagnostic commands to the PCI card 112 and enabling and disabling particular inputs and outputs of the PCI card 112. In an embodiment of the invention, the PCI API 212 are sufficiently generalized such that the PCI card 112 can be replaced by a different PCI card that includes a different set of input/output interfaces without requiring replacement of the presently installed kernel mode drivers 204—though reconfiguration may be required to set up new connections between the kernel mode drivers 204 and sources and recipients of data and commands in the PCI interface 202.

The kernel mode drivers 204 also includes functional components that respond to interrupts generated by the PCI card 112 (e.g., data ready, hardware errors, etc.). Other exemplary functions performed by the functional components of the kernel mode drivers 204 include detecting PCI installed devices, retrieving information about installed devices, read/write data from/to PCI configuration registers, execute a single read/write operation to an I/O port or memory on the PCI interface 202, set up interrupt handling, allocate resources, and store sensor device-specific data. The functional driver module 214 responds to new data available for submission to user mode processes (described herein below) responsible for rendering input data that drives the user mode graphical user interface (e.g., graphs, instantaneous parameter values for pressure and flow velocity, etc.).

The user mode level of the host 100 embodies a modular/component based architecture. The modular architecture provides a high degree of flexibility in developing and incorporating new sensor types, and corresponding graphical user interfaces, into the multimode host user interface. The user mode processes 206 include an extensible COM-based host application 222 that is responsible for presentation of a multiple interface mode graphical user interface (preferably with touch screen functionality). At startup, the host application 222 instantiates a set of user interface mode objects from a registry of available user interface mode object classes. Examples of such user interface mode objects include Pressure, Flow, and Combination. Extension of a base set of graphical user interfaces to include new user interface modes, such as Temperature and pH, is achieved by installing one or more new DLLs containing a user interface mode class objects corresponding to new user interface modes. In an embodiment of the invention, a separate user interface mode component object is provided for each distinct user interface mode supported by the host application 222.

The set of user mode processes 206 also include a set of measurement processing components 224. In an embodiment of the invention, each measurement processing component corresponds to a particular sensor. The measurement processing components 224 are instantiated from a set of sensor-specific component object model (COM) objects provided by one or more dynamically linked library (DLL) files. Each sensor-specific component is executed as a thread within a same process, or alternatively, as a separate process. Thus, a malfunction in one sensor-specific component will not affect the operation of properly operating sensor-specific components. The above-described COM approach to sensor data handling at the user mode level 206 also enables the set of input sensors and corresponding displayed interfaces to be readily extended by installing new DLLs from which the host system 100 instantiates COM objects corresponding to the new sensor input types. The illustrative host system 100 depicted in FIG. 2 includes the following sensor-specific components: pressure 226, flow velocity 228, flow volume 230, temperature 232, and auxiliary 234. An exemplary input processed by the auxiliary component 234 is a position signal rendered by one or more displacement sensors (e.g., a rotational position, a lengthwise position along a vessel). The sensor-specific components are described further herein below. Additional component types of components in the set of measurement processing components 224 (e.g., temperature, pH, etc.) in accordance with alternative embodiments of the host system 100.

In the illustrative embodiment of the invention, the set of sensor-specific components is extensible. Thus, when a new sensor type of sensor is developed for the host system 100, the set of measurement processing components 224 is extended by developing and dynamically incorporating a new sensor-specific component object. Thereafter, integration of the new sensor-specific component object is achieved by properly identifying the object as a member of the class of sensor-specific measurement processing components 224 that are instantiated when the system 100 starts up.

The set of measurement processing components 224 receive sensor data retrieved from the PCI interface 202 and drive inputs to particular ones of the graphical user interface display modes supported by the host application 222. The communications with the kernel mode processes 204 are carried out via a sensor component API 238 Which enables the measurement processing components 224 to communicate with an application logic component 240. The sensor component API 238 methods are function oriented. An exemplary set of such methods in the sensor component API 238 include: setting operational states of the sensors, extracting sensor data, issuing control commands to the PCI card 112 configuring/controlling operation of sensors. The application logic component 240 translates calls issued by ones of the set of measurement processing components 224 into calls to the kernel mode drivers 204. The application logic component 240 passes sensor data (originating from the PCI interface 202) from the kernel mode drivers 204 to the measurement processing components 224. Communications between the application logic component 240 and the kernel mode drivers 204 accessing the DSP 200 and the PCI interface 202 are carried out in accordance with a digital signal processing (DSP) API 242. The methods of the API 242 are hardware oriented, and include, by way of example: handling an interrupt, writing DRAM, writing DRAM, starting and stopping particular DSP functions relating to particular sensors and/or interfaces.

Having described the general architecture of the host system 100, attention is now directed to the multi-mode graphical user interface supported by the host application 222. It is further noted that the user interfaces preferably are augmented by touch screen functionality. The various display interface modes, while different, preferably share a common look and feel based upon a generic graphical user interface specification. FIG. 3 depicts an exemplary generic graphical user interface specification upon which a set of to graphical displays are based in accordance with the various graphical user interface modes supported by the host application 222.

The exemplary graphical user interface architecture consists of three dedicated data display regions. A first region 300 is reserved for display of system and patient information. A second region 302 is reserved for system messages. A third region contains a set of hierarchical screens including a set of functionally related display and interactive components accessed, by way of example, by selection of one of a set of tabs 306.

The first region 300 is persistent and is displayed during all modes of operation of the host application 222. In an embodiment of the invention, the first region 300 includes one or more of the following fields relating to a patient/session: Patient Name, Patient ID—customer specific identification number, Physician—name of the attending physician, Institution—name of the client institution using the system, Date/Time—current date and time, and a branding logo.

The second region 302 of the exemplary graphical user interface general layout is reserved to display system messages. The second region 302 also persists for all modes of operation. The second region 302 includes, by way of example, the following fields relating to the display of messages generated by the host system: Current status—a message indicating the current operation state or status of the unit; Warning events—a message advising the user of a potential problem and possible remedy; Error events—a message notifying the user of a system error and possible corrective action; and System Mode—a message notifying a user of the current mode of operation of the host 100.

A third region 304, by way of example, is reserved to display parameters and input/output data fields according to a current mode of operation of the host 100 and display mode of the host application 222. The third region 304 is not persistent. Rather, the content of the third region 304 is determined by a particular use mode within which the host application is operating. In an embodiment of the invention, the third region 304 operates in one or more of the following modes: System, Pressure, Flow, and Combo (Combination). Additional modes are supported/displayed by the host application 222 in accordance with alternative embodiments of the host 100. Such additional modes accommodate, for example, displaying additional sensor-provided/derived output parameters (e.g., temperature, pH, etc.) or new sets/combinations of previously existing output parameters display elements. Each mode includes at least a second level of screens once the mode is selected by means of the tabs 306.

Figure 4:
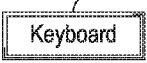
FIG. 4 depicts an exemplary graphical user interface for a patient data entry sub-screen of a system display mode of the host system.
Figure 5:
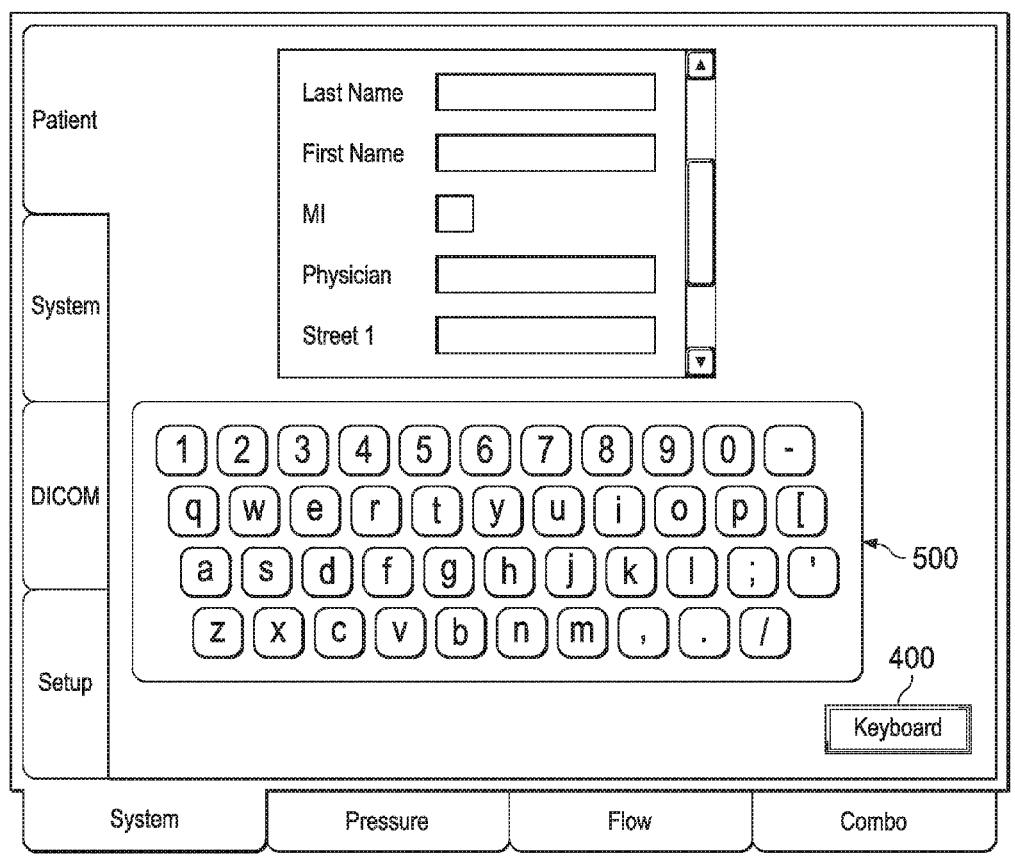
FIG. 5 depicts an exemplary graphical user interface for a user/patient data entry sub-screen of a system display mode of the host system that includes a keyboard.

Turning now to FIG. 4, an exemplary graphical user interface is displayed that is suitable for entry of patient information in accordance with the System mode of operation of the host application 222. In particular, the displayed graphical display corresponds to a user (patient) data entry sub-screen under the System mode. While the host 100 supports input of data using traditional keyboard, in an embodiment of the invention, the user enters, edits, and/or deletes patient information via a touch screen keyboard called up by selecting the keyboard button 400. Turning briefly to FIG. 5, in response to a user selecting the keyboard button 400, the graphical user interface depicted in FIG. 4 is modified to include a touch screen keyboard 500. Alternatively, keyboard 500 is provided automatically. The information entered will persist for the duration of the current session. The Patient/System Information Display area (the first region 300) reflects changes in corresponding fields.

Figure 6:
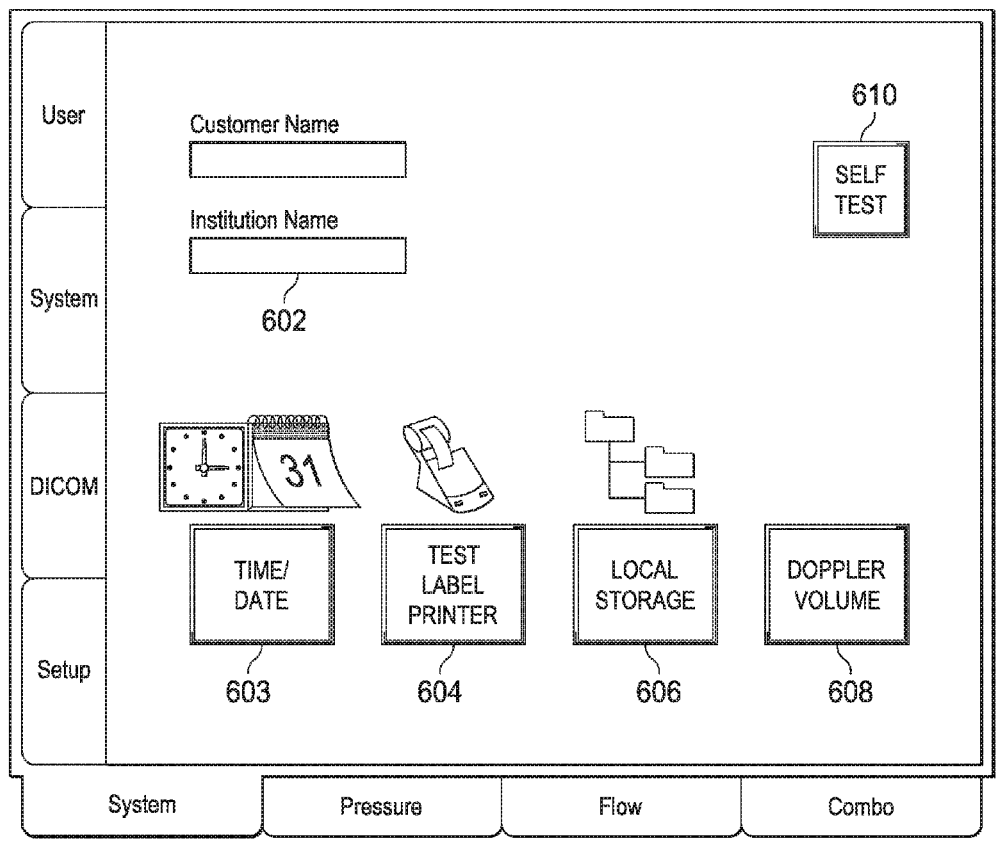
FIG. 6 depicts an exemplary graphical user interface for a system configuration sub-screen of a system display mode of the host system.

FIG. 6 comprises an exemplary system sub-screen under the System mode. The user enters relevant system information, e.g., customer/institution name 602, time/data 603, printer 604, LAN connection, local data storage 606, and/or a Doppler audio volume 608. The system sub-screen depicted in FIG. 6 preferably also includes a button/control 610 enabling a user to initiate, a system self-test. The user specified information/configuration persists indefinitely and spans multiple patient sessions. The Patient/System Information Area (the first region 300) reflects changes entered via this interface.

Figure 7:
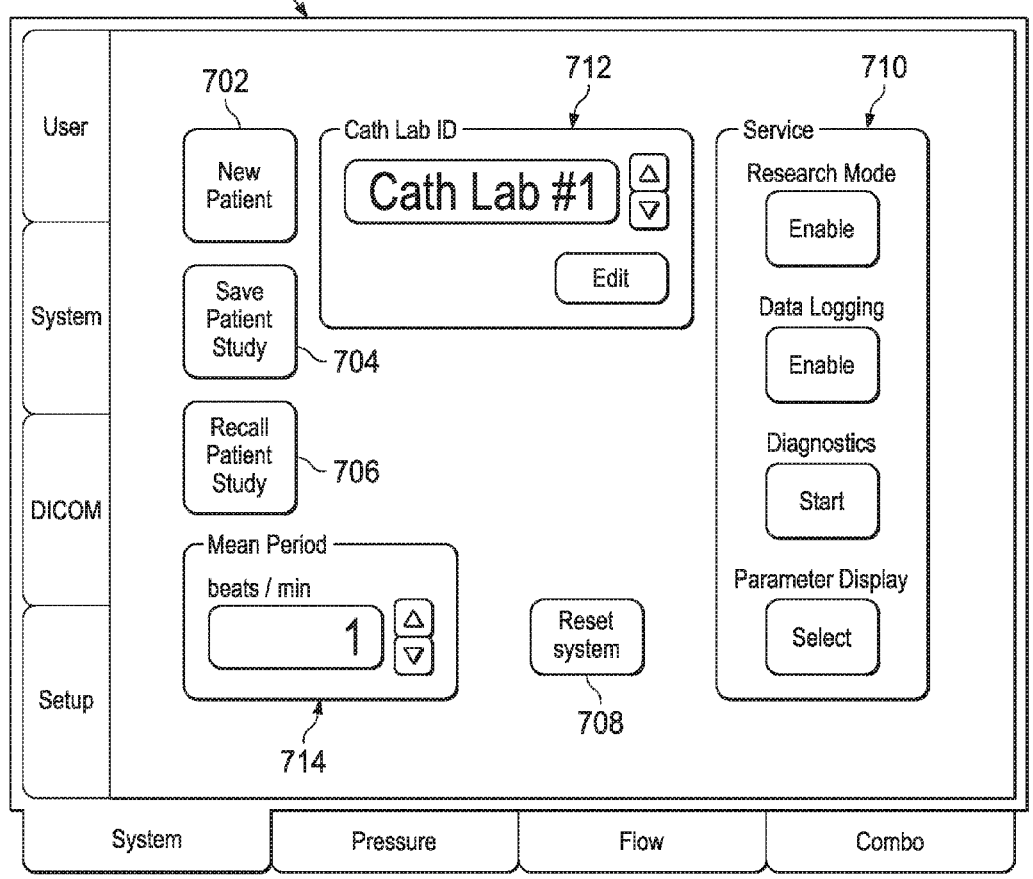
FIG. 7 depicts an exemplary graphical user interface for a setup sub-screen of a system display mode of the host system.

FIG. 7 comprises an exemplary system setup sub-screen 700 under the System mode of the host application 222. While the system setup interface enables a user to modify default settings, the new default settings are stored in a non-volatile file, persist indefinitely, and span multiple patient sessions. The default settings are applied on system startup and reapplied via a reset button. As depicted in FIG. 7, the system setup sub-screen includes a new patient button 702 that invokes an interface enabling a user to enter new default setting for a new patient. A save patient study button 704 enables a user to store a session to a persistent device. A recall button 706 invokes an interface enabling a user to review and recall stored sessions. A reset system button 708 when selected, resets system information to default settings. A series of service selection buttons 710 enable a research mode of operation of the host system 100, enable data logging, commence diagnostics on the host 100, and enable selection of parameters displayed. A Cath Lab ID 712 allows the specification of a previously stored particular configuration/setup based, for example, upon a particular catheter lab within which the host 100 is to based. However, the Cath Lab ID 712 field can be used to recall settings of any particular previously stored configuration/set up of the host 100. A mean period field 714 allows an operator to designate the number of cardiac cycles that are used to calculate a single average value (e.g., Average Peak Velocity).

Figure 8:
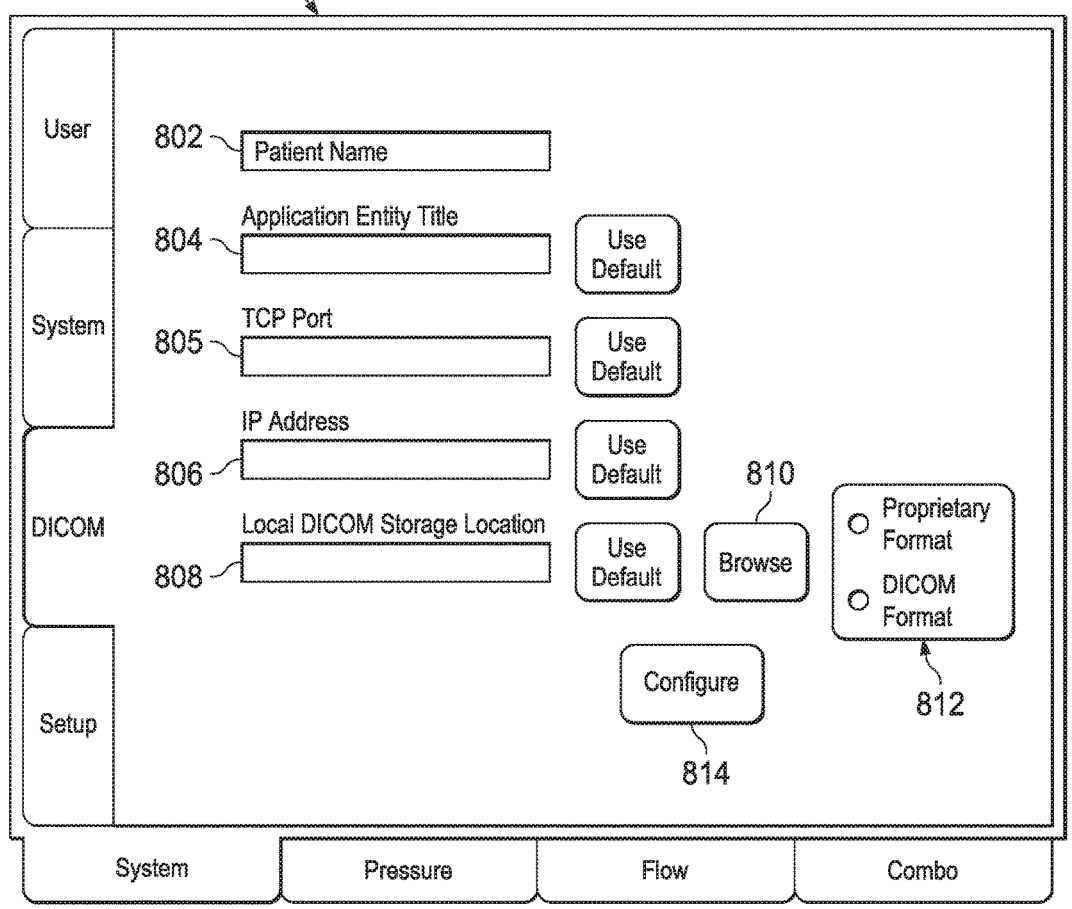
FIG. 8 depicts an exemplary graphical user interface for a communications sub-screen of a system display mode of the host system.

FIG. 8 comprises an exemplary network communications setup sub-screen 800. In the exemplary embodiment, the sub-screen enables a user to provide information regarding report storage and transfer, connectivity, and format. In the exemplary embodiment a user interfaces to a DICOM (Digital Imaging and Communication in Medicine, an exemplary format for data exchange between two different systems) compliant information management system via the DICOM sub-screen 800 interface of the system mode of the host application 222. Other services provided by the DICOM sub-screen interface include transferring images to a remote DICOM archive and recalling images from the remote DICOM archive. The fields of the sub-screen 800 include a patient name 802, an application entity title 804 for specifying the DICOM nodes with which the host 100 communicates, a TCP port field 805 specifies a port through which communications will take place, an Internet protocol address 806 identifying the address of the computer on the network with which the host 100 communicates, local DICOM storage location 808 specifies the local directory where the host 100 stores DICOM files, a browse button 810 launches a well known utility to search within the host 100's directory structure or create a new directory, storage file format 812 enables a user to select a file storage format (e.g., DICOM, proprietary, etc.), and a configure button 814 launches configuration of the communications based upon the specified field data.

Figure 9:
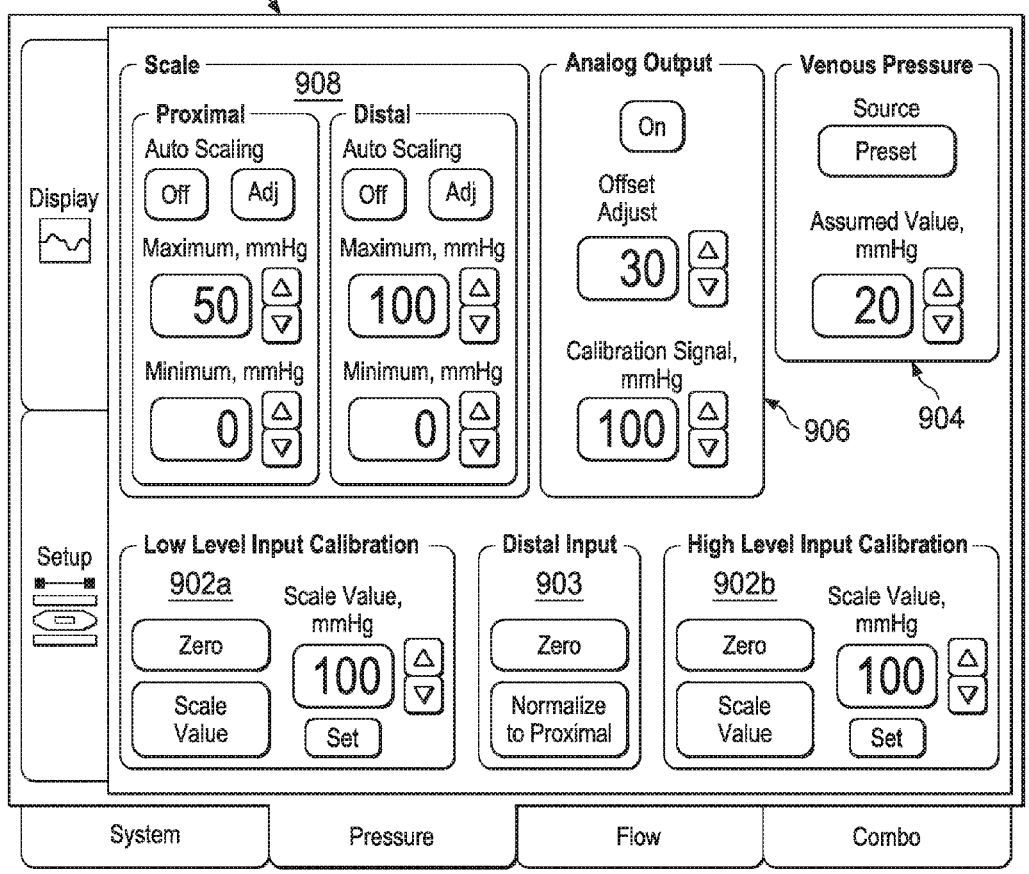
FIG. 9 depicts an exemplary graphical user interface for a setup sub-screen of a pressure display mode of the host system.

An exemplary set of interfaces associated with the system (administrative) mode of operation of the host system 100 including the host application 222 has been described. Attention is now directed to a set of diagnostic modes of operation of the host system 100, and more particularly the display interfaces associated with illustrative pressure, flow and combination modes of operation. With reference to FIG. 9, the host application 222 includes a pressure mode setup sub-screen 900 that enables a user to specify particular display attributes associated with a display sub-screen (see FIG. 10). The pressure setup sub-screen 900 preferably provides the user with input features to customize the operation of the pressure mode.

The illustrative pressure mode setup sub-screen 900 includes a set of low and high level input calibration controls 902a and 902b enabling a user to calibrate a pressure sensor in a variety of ways. The zero button in the calibration control displays 902a and 902b facilitates establishing a zero reference for the pressure sensor and a zero output level reference for any external instruments. Zero level calibration is performed by applying a zero pressure (ambient) and selecting the zero button on the calibration controls 902a and 902b. By way of example, low level input calibration is achieved through the low level input calibration control 902a by applying a low pressure input, setting adjusting the scale value to the input pressure, and then pressing the set button. A high level input calibration is achieved through the high level input calibration control 902b by applying a high pressure input, setting adjusting the scale value to the input pressure, and then pressing the set button.

Though not shown in FIG. 9, the low and high pressure calibration is alternatively performed by pressing the button labeled "scale value" to enable calibration by establishing a zero pressure and providing a "slope" or calibration factor defining the relationship between changes to the input pressure and the input signal. The button labeled "scale value" actually toggles the calibration mode, and in response the calibration display 902a or 902b converts to a calibration factor mode. Rather than supplying an actual pressure, instead a calibration factor expressed in terms of micro-volts per mmHg is entered by adjusting a displayed value and then pressing the set button.

The pressure mode setup sub-screen 900 also includes a distal input normalization control 903 for normalizing input pressure measurements from a distal pressure sensor via touch screen button controls. Normalization is the matching of the guide wire pressure sensor reading with an aortic pressure. Normalization is achieved by bringing the pressure sensor to an appropriate, location and selecting the normalization button. This establishes a new value for the aortic pressure that is used to determine various calculated/displayed output parameter values, including FFR. A distal sensor zero reference is established by selecting the zero button in the distal input normalization control 903 while applying a zero pressure reference.

The pressure mode setup sub-screen 900 also includes a set of venous pressure controls 904 including a venous pressure source control and venous pressure adjust (up/down) controls. A mean venous pressure value enables computing an FFR. The mean venous pressure may be input from a transducer via an external monitor or by a user preset value. Selecting the venous pressure source button on the setup sub-screen 900 toggles the source. Selecting 'External' designates the venous pressure source as a patient-applied transducer through an external monitor. Selecting 'Preset' allows the user to enter an assumed value. Selecting the up/down controls increases/decreases the preset value accordingly. The preferred range of values for the venous pressure is about 0-50 mmHg.

An analog output offset adjust 906 provides an interface for a user to adjust the offset and the pressure high level analog output of the host system 100. The user can increase or decrease the output via the user interface. The output displays the current output adjustment level via the user interface. The analog output is modified accordingly. Change is effected by selecting the Up/Down arrow buttons adjacent to the Offset Adjust display to increase/decrease the value accordingly. The value will change, for example, in steps of 1 mmHg. The preferred range of values is about −30 to 330 mmHg.

The setup sub-screen 900 also includes maximum/minimum scaling presets 908 for both distal and proximal pressures. An on/off button enables/disables an autoscaling feature of the host graphical output display for the proximal and distal pressures. When autoscaling is activated, the scale of the output display expands as needed to handle an increased range of output pressures. A toggle button displayed in the "adjust" state for both proximal and distal scaling, enables manual adjustment of the maximum and minimum scale values using the up/down arrow buttons. The pressure graph depicted in FIG. 10 in the display sub-screen for the pressure mode reflects the designated scales.

Figure 10:
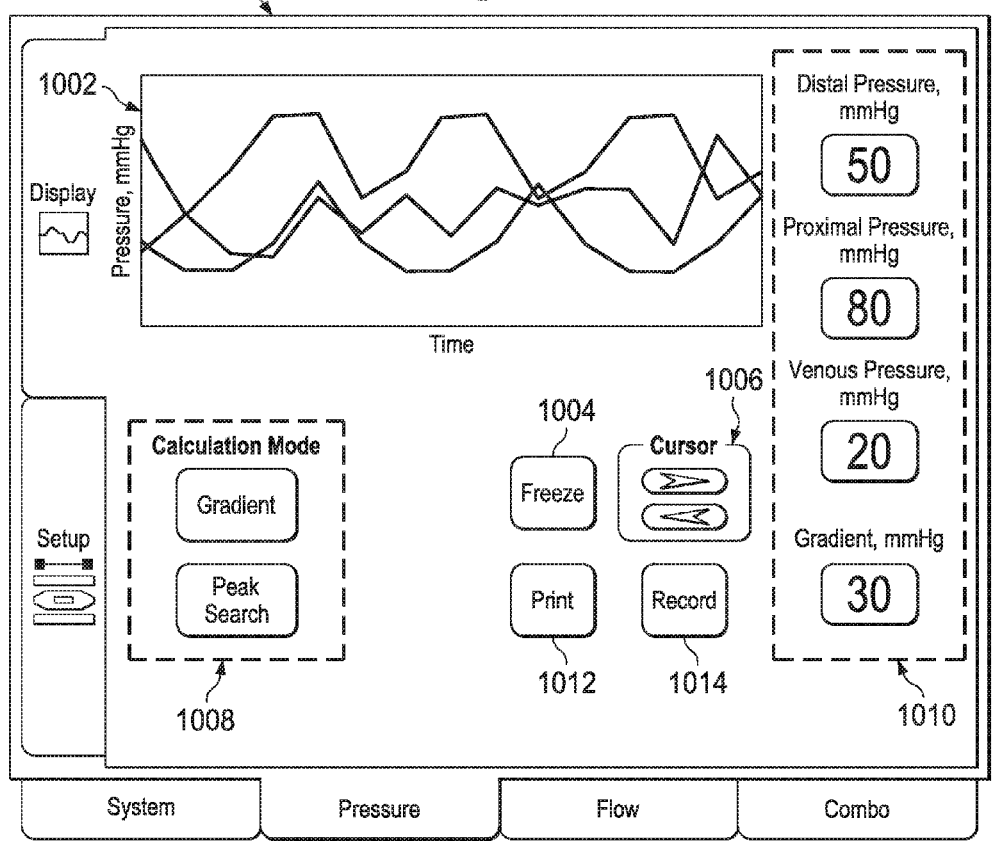
FIG. 10 depicts an exemplary graphical user interface for a display sub-screen of a pressure display mode of the host system.

Turning to FIG. 10, an exemplary pressure mode display sub-screen 1000 displays data and pressure mode controls. The data driving the pressure display is supplied by the pressure component 226 of the set of measurement processing components 224 identified in FIG. 2. The exemplary pressure mode display sub-screen 1000 includes a pressure waveform graph 1002 including multiple pressure waveforms including distal, venous, and aortic pressure waveforms. A run/freeze control 1004 stops and starts scrolling.

A cursor/position control 1006 facilitates searching a waveform. A calculation mode control 1008 includes a first button for selecting a pressure calculation mode (e.g., distal/proximal gradient, distal/proximal ratio, normalized pressure ratio (NPR), and fractional flow reserve (FFR)) and a second button to search for peaks (visible only in FFR mode and used to detect peak hyperemic response after injecting a hyperemic agent). When the calculation mode control 1008 is selected, it changes to a next one of the available types of calculation modes. The exemplary pressure display sub-screen 1000 also includes a set of instantaneous/current measurement digital displays 1010 including: distal pressure, aortic pressure, venous pressure; and a selected calculated value (e.g., distal-to-proximal gradient, distal-to-proximal ratio, NPR, FFR). A print button 1012 initiates printing a set waveforms recorded during a session. Recording of the waveforms is toggled on/off by means of the record button 1014.

In the illustrated display, gradient calculation mode has been selected. In an exemplary embodiment, a gradient output is measured by taking a difference between pressures before (e.g., aortic) and after a partially blocked vessel. The distal-to-proximal ratio is calculated by dividing the distal pressure by the proximal pressure. The normalized pressure ratio is calculated by subtracting the venous pressure from the distal and proximal pressures and then taking their ratio. The FFR value is calculated by taking the normalized pressure ratio at the peak hyperemic response. Pressure gradients/ratios across a heart valve are also provided in association with yet another potential calculated value rendered by the host 100.

Figure 11:
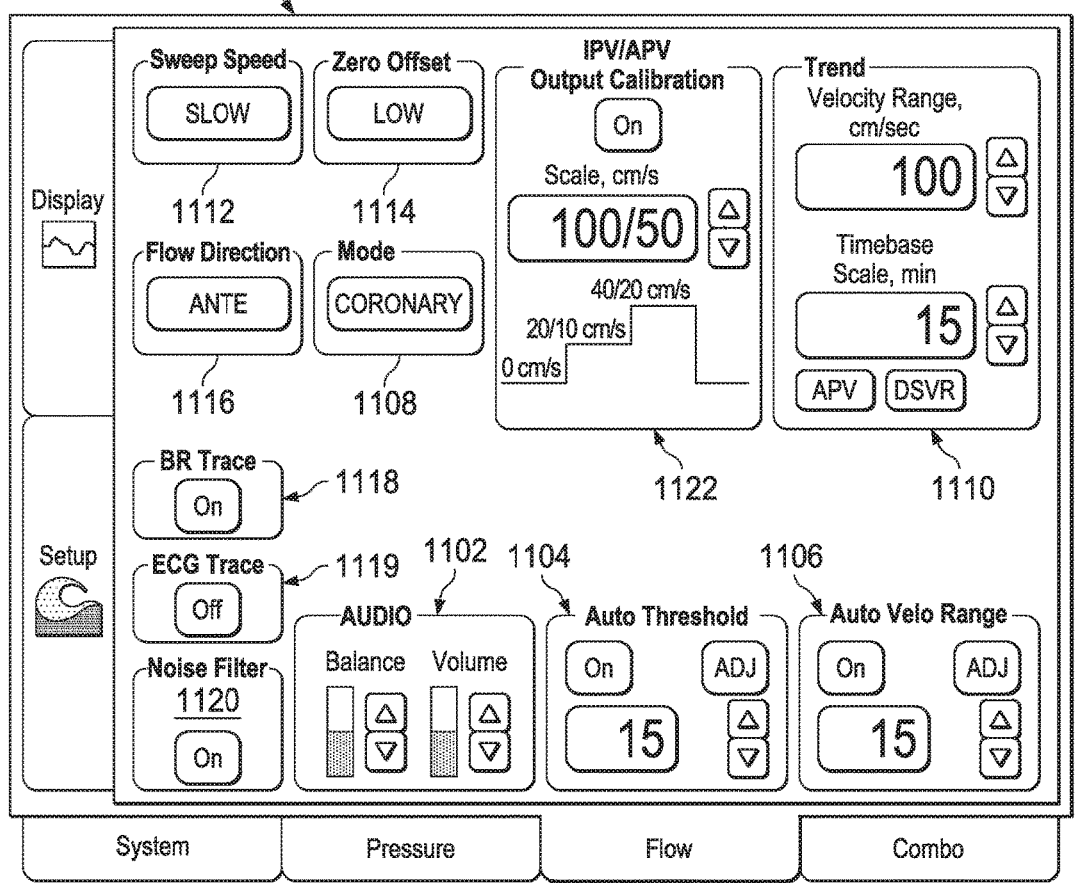
FIG. 11 depicts an exemplary graphical user interface for a setup sub-screen of a flow display mode of the host system.

Next, an exemplary set of user interfaces are show depicted that are associated with a flow mode of operation of the host 100 and host application 222. The flow mode graphical user interface is subdivided into a number of sub-screens illustratively depicted by way of example herein. With reference to FIG. 11, a setup screen 1100 provides the user with interface setup features to select and customize the operation of the flow mode of operation of the host 100. The flow setup includes controls to set for example: Doppler audio volume and balance 1102—for a set of stereo speakers, a signal threshold 1104—via an on/off button and a threshold adjust, and velocity range 1106—similar to pressure in that a user can select either auto ranging or manually adjust the maximum on the scale in the case where the auto ranging is shut off. A configuration button 1108 toggles between coronary and peripheral artery configurations to take into consideration the delay of velocity changes in relation to an ECG signal.

Trend setup controls 1110 set velocity scale and time base scale for a trend output. Furthermore, the trended parameter, average peak velocity or diastolic/systolic velocity ratio, is selected via the trend setup controls 1110. Other exemplary controls for the flow display mode include a sweep speed 1112 (selects the scrolling speed of the spectral display from 3 speeds: slow, medium, or fast), zero offset 1114 (selects the zero velocity baseline position from 3 locations: low, medium, or high), and a flow direction 1116 (select the direction of flow to be displayed above the baseline from 2 bearings: antegrade or retrograde). A user can also optionally designate whether to display a blood pressure trace 1118, ECG trace 1119. A user also selectively activates a noise filter 1120. A calibration section 1122 allows a user to enable/disable an output calibration signal and select the particular waveform for performing the calibration.

With reference to FIGS. 12*a-e,* a set of illustrative examples of a flow display are provided in accordance with two primary flow sensing configurations, coronary and peripheral—as designated by the configuration button 1108 on the flow setup sub-screen depicted in FIG. 11. A flow operation sub-screen 1200 is displayed in its depicted state when a CFR operation button 1201 button is selected. In response, a multi-partitioned waveform display depicts a full wave form graph 1202 as well as two smaller waveform display output segment graphs 1204 and 1206 corresponding to the base waveform and peak wave form (under hyperemic conditions). The designation of the time frame in which data is gathered and displayed within the graphs 1204 and 1206 is determined by pressing the base/peak button 1208 a first time to acquire the base readings and then pressing the base/peak button 1208 a second time to acquire the peak readings.

The graphs 1202, 1204 and 1206 display flow velocity (based upon flow velocity input data in the form of Doppler spectral arrays), measured in a variety of ways (e.g., average peak velocity, mean peak velocity and flow velocity). At each point in time, a set of grayscale values are assigned to each representative frequency component of the display. Intensity is assigned to points along a same time slice on the graph based upon prevalence of the frequency indicative of blood flow velocity. The display generates a set of markers associated with particular sensed events. For example, the "S" represents the systolic pressure reading while the "D" represents the diastolic pressure reading in a cardiac cycle. A user can limit the displayed spectra by adjusting the threshold background 1104 to exclude low level frequency components. Simultaneous with the velocity spectra, an instantaneous peak velocity tracking the blood flow velocity envelope's peak may also be displayed.

In the illustrative embodiment, instantaneous/current calculated values for graphed parameters are digitally displayed as well in field 1210. In particular, field 1210 displays the instantaneous heart rate, average peak velocity (APV), and diastolic/systolic velocity ratio (DSVR). Additional subfields of field 1210 depict the APV and DSVR determined during a designated base time span and peak time span. Field 1210 also displays the CFR calculated from the base and peak values. An optimal wire position indicator 1212 visually prompts a user to move the wire to obtain optimal placement positioning. A run/freeze button 1214 starts and stops scrolling of the displayed waveforms, and a cursor 1215 allows scrolling within the previously displayed sections of the waveforms. A print button 1216 enables the printing of the waveforms. A record button 1218 toggles a data/waveform recorder between an active/inactive legging state.

Having described an exemplary interface associated with the CFR flow mode, attention is briefly directed to other coronary modes supported by the exemplary host system 100. FIG. 12*b* depicts the display of the host system 100 when a user selects the proximal/distal button 1220 while in the coronary flow configuration. Instead of the base/peak button 1201, a proximal button 1222 and a distal button 1223 are displayed.

The proximal button 1222 is selected to invoke pressure input processing by the host system 100 corresponding to a pressure observed proximal (before) a stenosis. The corresponding waveform is displayed upon a graph 1224. The distal button 1223 is selected to invoke pressure input processing corresponding to a pressure observed distal (after) a stenosis. The corresponding waveform is displayed upon a graph 1226.

The output display depicted in FIG. 12*b* includes instantaneous/current calculated values for graphed parameters in field 1228. In particular, field 1228 displays the instantaneous heart rate, average peak velocity (APV), and diastolic/systolic velocity (DSVR). Additional sub-fields of field 1228 depict the APV and DSVR determined for proximal and distal pressure readings. Field 1228 also displays the proximal/distal ratio calculated by the host 100 from the observed proximal and distal pressures.

FIG. 12c depicts a graphical output display rendered in accordance with trend calculations supported by the host system 100. When the trend operation is selected, the host system 100 calculates an average flow velocity value (e.g., APV, DSVR, etc.) over a period of time (e.g., a cardiac cycle) and visually renders the value in the form of a graph. 1230. The trend mode is entered when a user selects a trend button 1231. In response, an APV button 1232 and a DSVR button 1234 are displayed. Based Upon a user's selection, the calculated and displayed average is either an APV or a DSVR. It is noted that the above two trend parameters are merely exemplary as those skilled in the art will readily appreciate that other input/calculated are suitable for trend calculation, display and analysis.

Figure 12A:
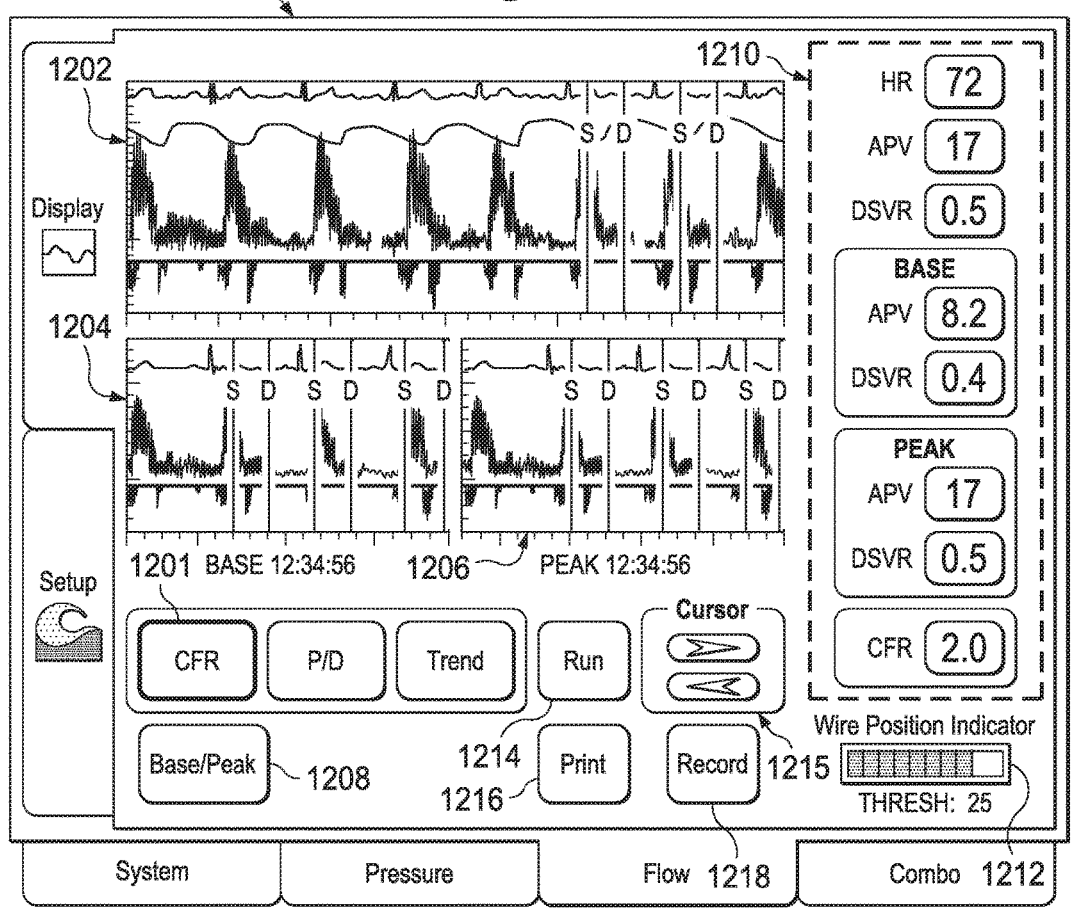
Figure 12E:
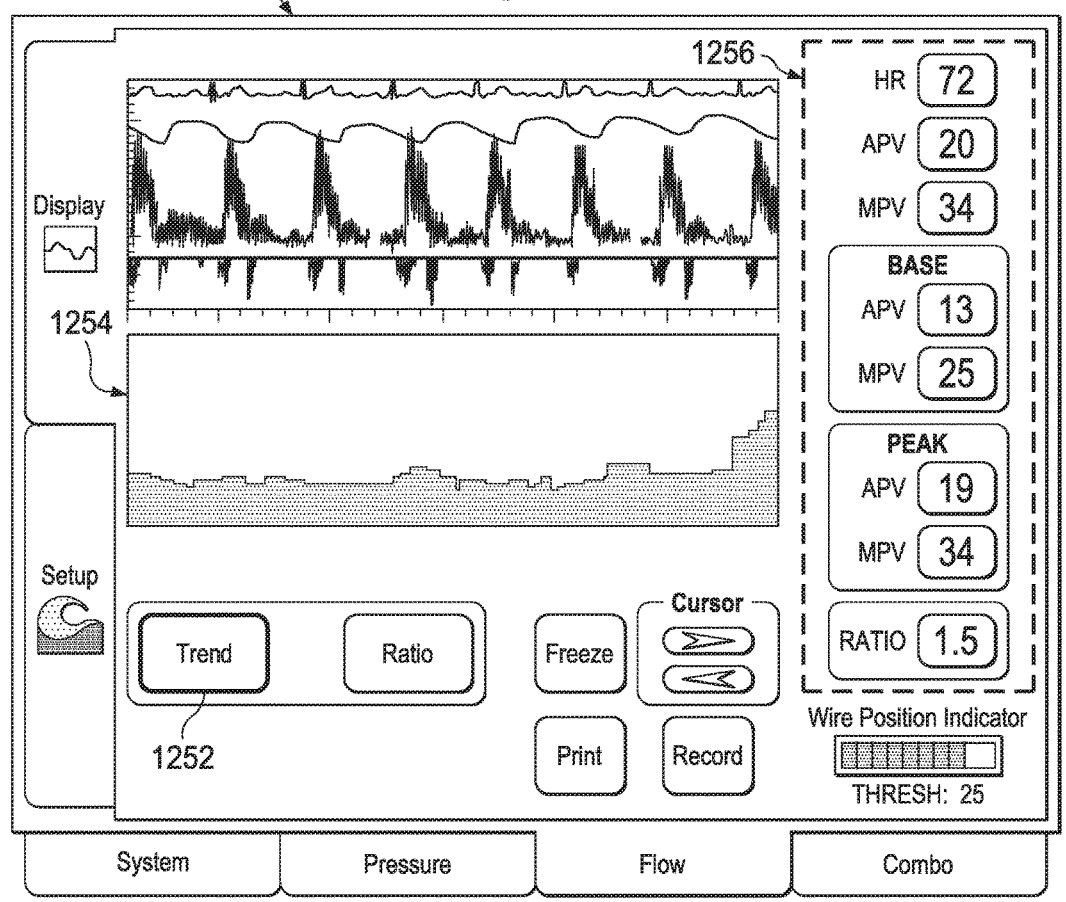

With continued reference to FIG. 12e a set of instantaneous/current calculated values for graphed parameters are digitally displayed in field 1236. The output parameters displayed in field 1236 are the same as the ones depicted in field 1210 in FIG. 12a. However, the BASE, Peak and CFR parameters are not calculated by the host 100 while trend analysis is occurring. Rather, these parameters are retrieved, if they exist, from previous calculations rendered when the user selects the CFR button 1201. The base value is marked in the trend graph 1230 with a "B", the peak value with a "P", and the starting point of the peak search with an "S". The time scale of the trend graph 1230 is on the order of one or multiple minutes. The time scale of the ECG graph above the trend graph is on the order of seconds.

Turning now to FIGS. 12d and 12e, graphical display outputs are illustratively depicted for two exemplary peripheral operations supported by the host 100. These two sub-screens of the flow mode graphical display 1200 are entered by selecting the peripheral configuration through the coronary/peripheral configuration button 1108 on the flow setup sub-screen depicted in FIG. 11. The peripheral configuration takes into account that, in peripheral arteries, a flow velocity signal lags an ECG signal, and therefore the peripheral configuration introduces a time shift to account for the lag.

FIG. 12d illustratively depicts the display 1200 when the ratio button 1240 is selected while the host system 100 is in the peripheral flow configuration. A graph 1242 displays a continuous graph depicting calculated flow velocity. A base flow velocity graph 1244 is rendered from data collected by the host system 100 after a base/peak button 1246 is selected a first time. A peak flow velocity graph 1248 is rendered from data obtained after the base/peak button 1246 is selected a second time.

In the illustrative embodiment, instantaneous/current calculated values for graphed parameters are digitally displayed as well in field 1250. In particular, field 1250 displays the instantaneous heart rate, APV, and mean peak velocity (MPV). Additional sub-fields of field 1250 depict the APV and MPV determined during a designated base time span and peak time span. Field 1250 also displays a ratio calculated from the base and peak values.

FIG. 12e illustratively depicts the display 1200 when the trend button 1252 is selected while the host system 100 is in the peripheral flow configuration. The two snapshot graphs 1244 and 1248 are replaced by a single trend graph 1254. In the illustrative embodiment, instantaneous/current calculated values for graphed parameters are digitally displayed as well in field 1256. In particular, field 1256 displays the instantaneous heart rate, APV, and mean peak velocity (MPV). Additional sub-fields of field 1256 depict the APV and MPV determined during a designated base time span and peak time span. Field 1256 also displays a ratio calculated from the base and peak values. However, the displayed Base, Peak and ratio values in field 1256, are provided from the previously described ratio operation described with reference to FIG. 12e.

Figure 13:
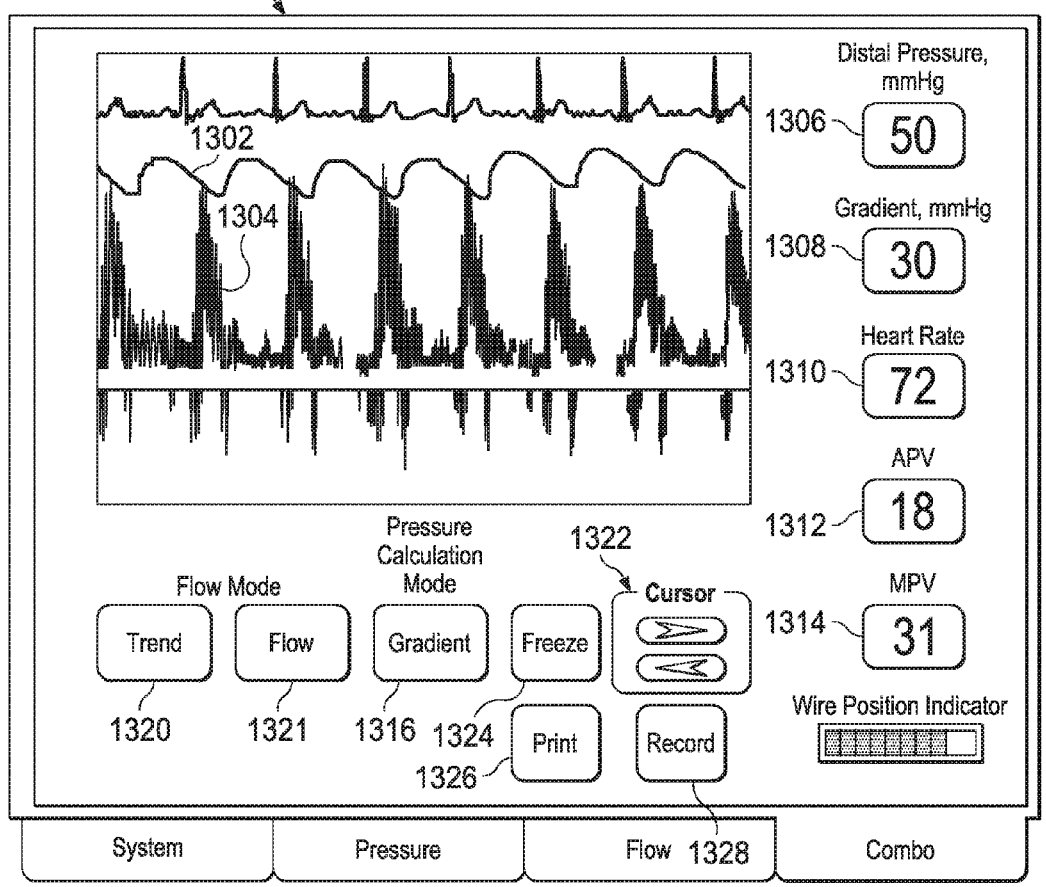
FIG. 13 depicts an exemplary graphical user interface for a combination flow and pressure display mode of operation of the host system.

Yet another exemplary mode of the multiple interface modes is a combination mode that provides data from multiple sensors in a single graphical interface. In the illustrative example, no new signal input types are needed to carry out the illustrative combination type of graphical display interface. In alternative embodiments, the combination mode includes additional sensor input types such as, for example, a temperature input or a position sensor. FIG. 13 provides an exemplary combination mode display in which flow and pressure measurements are combined to render two side-by-side scrolling graphs depicting sensed flow and pressure parameters during an invasive diagnostic procedure wherein a flexible elongate member such as a guide wire, configured as a combination device (in this particular case including both a pressure sensor and a Doppler flow sensor) is inserted into a patient. Such combination devices, used in association with the combination output provide a desirable environment in which to calculate fractional flow reserve (FFR) using pressure readings, and coronary flow reserve (CFR) using flow readings. However, it is possible to utilize the present system to make CFR and FFR measurements using non-combination devices, i.e. using multiple known single sensor devices.

Referring now to FIG. 13, the combination mode display screen 1300 includes a first graph 1302 of sensed pressure and a second graph 1304 of flow output parameters such as, for example, Doppler spectral arrays, average peak velocity and flow volume. Digital displays are provided that illustratively indicate instantaneous measurements for distal pressure 1306, a pressure calculation (based upon selected calculation via button 1316) such as gradient pressure 1308 (but also displays FFR or other calculated pressures), heart rate 1310, average peak flow velocity 1312 and mean peak flow velocity 1314.

A CFR/Trend button 1320 provided a user the capability of selecting a CFR operation or trend operation in association with the acquisition of flow data. A flow velocity button 1321 enables selection of a flow velocity output mode. As disclosed previously in FIGS. 10 and 12a-e the screen 1300, in an embodiment of the invention, reconfigures in association with a user's selection of the various selectable operations and calculations supported by the combination mode of the host 100.

The combination screen 1300 also preferably includes scroll controls in the form of scrolling arrows 1322 that enable a user to scroll forward and back along the graphical output. A freeze/run toggle button 1324 enables/disables scrolling of the graphs 1302 and 1304. A print button 1326 initiates printing a session (or portion thereof). A record button 1328 commences and halts recording session data in a toggling manner.

In addition to the touch screen controls, the host 100 preferably supports interactive remote control/selection of the various display components depicted in the exemplary graphical user interface displays described herein above.

Figure 14:
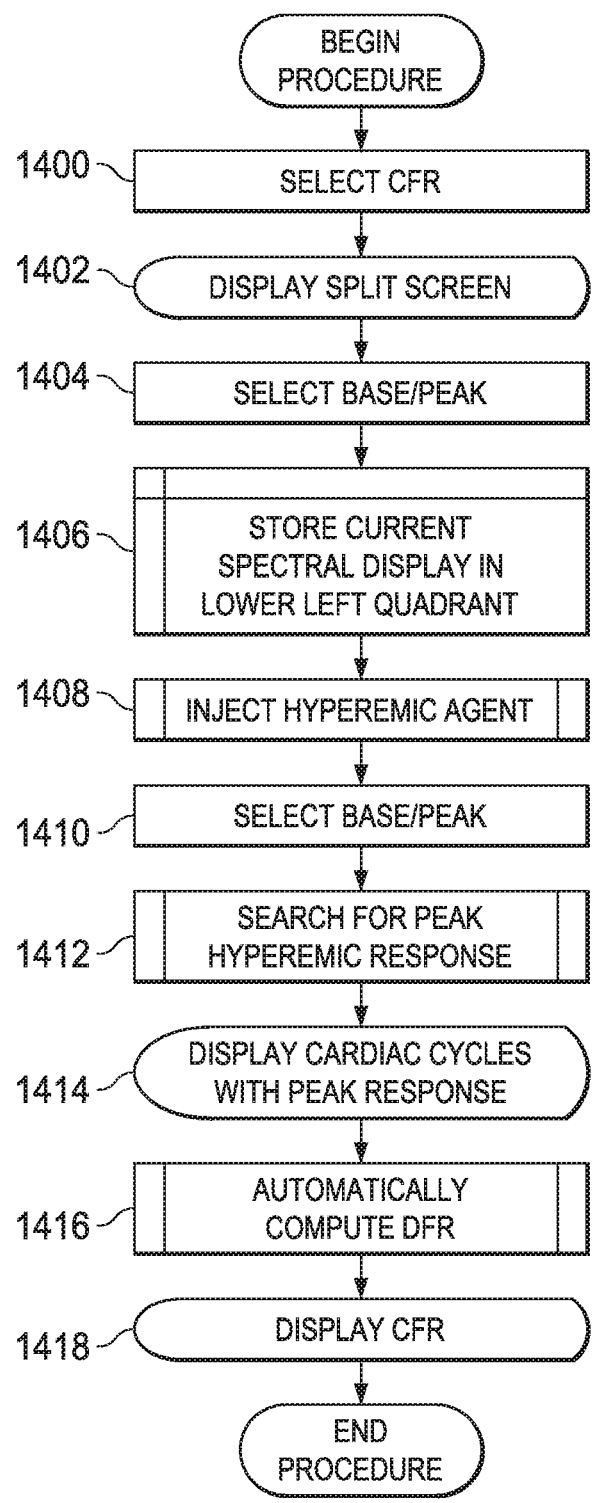
FIG. 14 is a flowchart summarizing a set of steps for carrying out a coronary flow reserve measurement using the multipurpose host system described herein.

Having described a set of exemplary graphical user interfaces associated with a host system 100 embodying the present invention, attention is directed to FIG. 14 which depicts a flowchart summarizing an exemplary set of steps for carrying out a coronary flow reserve (CFR) measurement. Initially, a user selects the flow interface mode of the host application 222. Thereafter, during step 1400 the user presses the CFR button 1201 on the display screen to measure CFR. In response during step 1402 the graph area of the screen 1200 vertically partitions into upper and lower halves. The upper half graph 1202 displays the real-time velocity spectra presently measured by the Doppler sensor. The lower half of the graph display area is divided horizontally into two sections for displaying snapshots of the spectral display taken from the upper partition. The lower left area contains baseline graph 1204, and the lower right area is reserve for a peak response graph 1206.

During step 1404, a user presses the BASE/PEAK button 1208 on the display 1200 to save the baseline spectral display. A snapshot of the real-time spectral display is transferred to the lower left (baseline) graph 1204 of the display during step 1406.

Next, at step 1408 a hyperemic agent is injected into the patient. At step 1410 the BASE/PEAK button 1208 is selected a second time. In response, at step 1412 the host application 222 automatically begins a search for a peak hyperemic response (maximum average peak velocity (APV)—where the APV is determined by averaging the instantaneous peak velocity (IPV) over a cardiac cycle). During step 1414 a snapshot of the real-time spectral display is transferred to the lower right (peak) area on the graph 1202. During steps 1416 and 1418 the CFR ratio is periodically recalculated based upon the maximum APV found during the search and the current maximum ratio is displayed digitally in field 1210. Pressing the BASE/PEAK button 1208 a third time manually terminates the search. The search is automatically terminated if 5 consecutive seconds have elapsed and the maximum APV has not changed. The last CFR ratio value is held in the display as the process for determining the CFR ratio ends.

Figure 15:
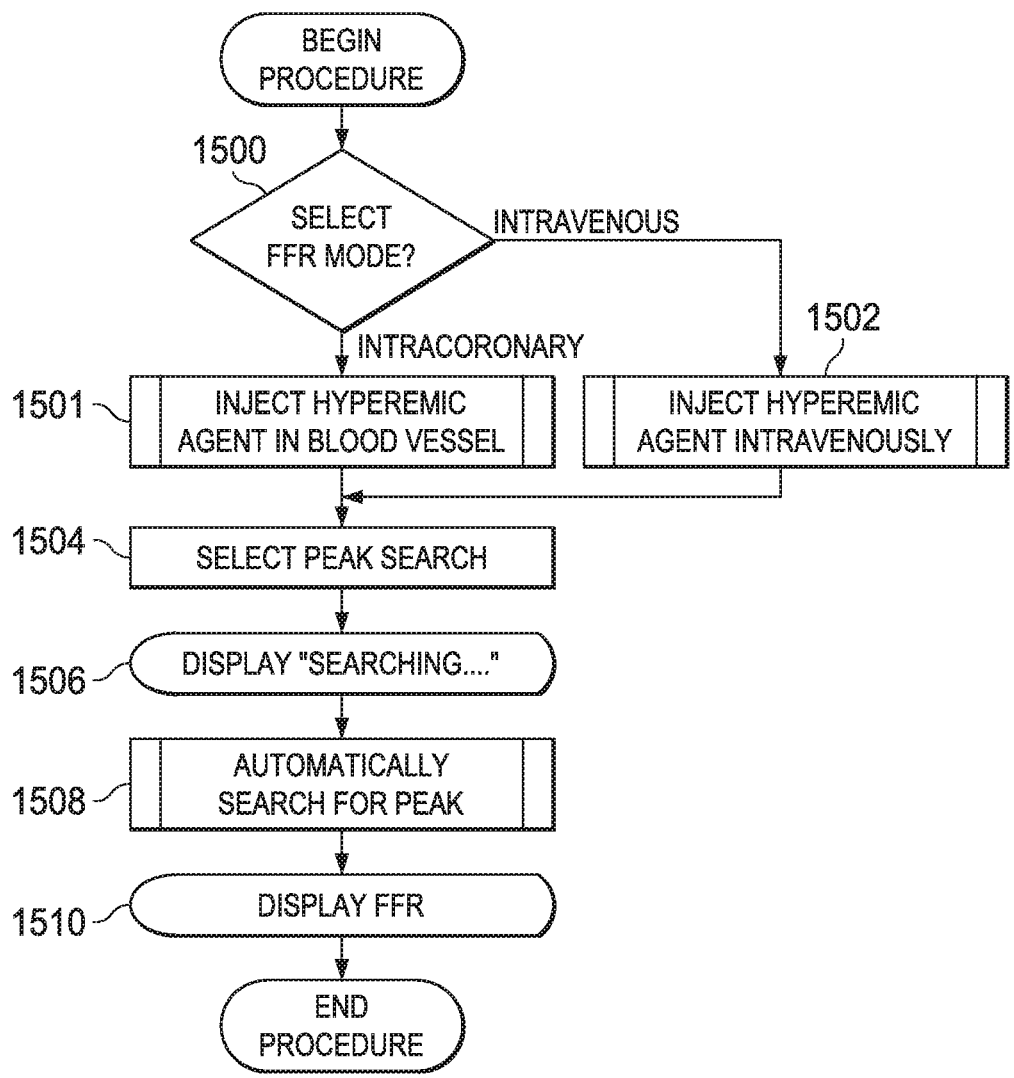
FIG. 15 is a flowchart summarizing a set of steps for carrying out a fractional flow reserve measurement using the multipurpose host system described herein.

Turning now to FIG. 15, an exemplary set of steps for carrying out a fractional flow reserve (FFR) determination using the host system 100 in a pressure mode and a guide wire including a pressure transducer is summarized. Initially, during step 1500 the FFR mode is selected via the calculation mode button of the calculation mode control 1008. A blood pressure sensor is placed in position to measure distal pressure within a vessel. Aortic pressure is simultaneously monitored using an aortic pressure sensor. Thereafter, during step 1501 or 1502 (based upon the specifically selected FFR mode—intracoronary or intravenous) the hyperemic agent is either injected in the blood vessel under investigation or administered intravenously. The peak search button of the calculation mode control 1008 (displayed only for FFR mode) is selected to observe the hyperemic response of the vessel during step 1504. The host application 222 displays a "searching" prompt at step 1506 until it locates a peak response while carrying out a search during step 1508. When the peak is detected, the FFR value is displayed during step 1510 on the display 1000.

Figure 16:
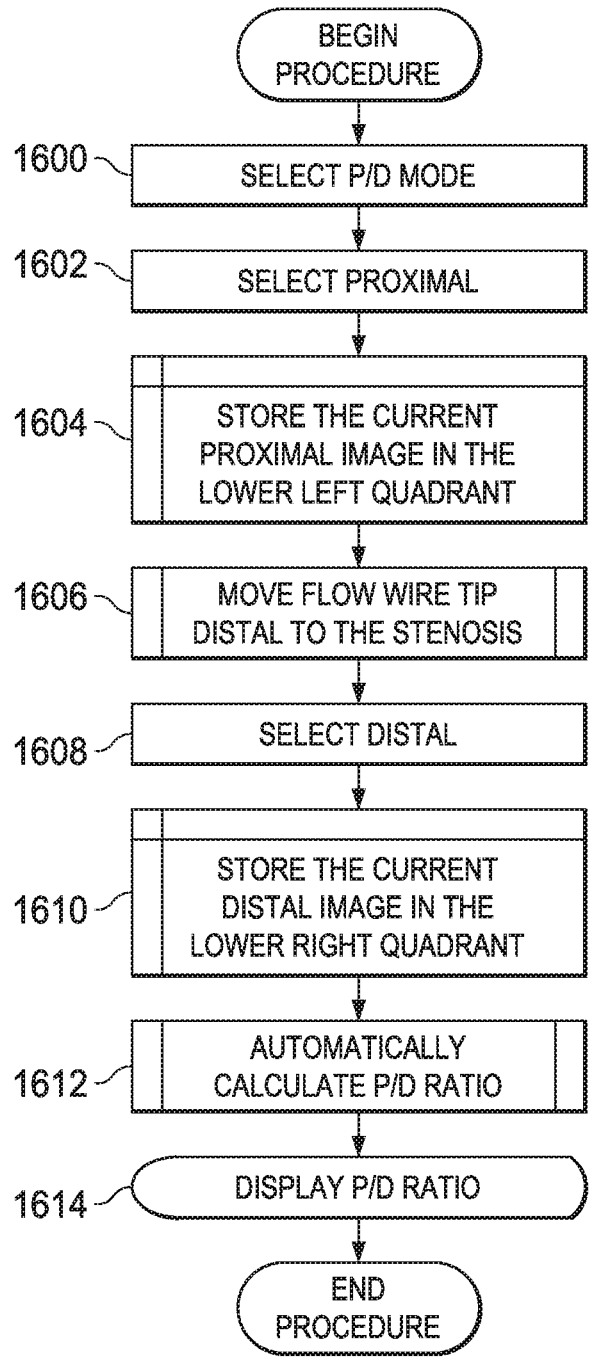
FIG. 16 is a flowchart summarizing a set of steps for carrying out a proximal/distal pressure ratio measurement using the multipurpose host system described herein.

The pressure mode of operation of the host application 222 preferably also supports determination of a proximal/ distal ratio. The set of exemplary steps for such a procedure are depicted in FIG. 16. Initially during step 1600 the P/D mode is selected via the calculation mode button of the calculation mode control 1008. This results in a split screen similar to the one described above for the CFR ratio determination process summarized in FIG. 14. Next, at step 1602 after moving a pressure sensor to a proper location within a vessel to obtain a proximal pressure reading, a user selects a proximal button that is displayed when the ratio calculation operation is selected. In response, during step 1604 the host application 222 stores the current proximal image in the lower left quadrant of the graph 1002 (in a split screen similar to the one displayed for CRF operations). Next, a pressure sensor of the guide wire is moved to a point beyond (distal to) a stenosis during step 1606. At step 1608 a distal display button rendered within the calculation mode control 1008 area is selected on the graphical display screen 1000. In response, during step 1610 the host application 222 stores the current distal image in the lower right quadrant of the graph 1002. At step 1612 the proximal/distal pressure ratio is calculated based upon the stored inputs at steps 1604 and 1610, and during step 1614 the P/D ratio is displayed on the display 1000. It is noted that the ordering of taking the proximal and distal readings is not important to carry out the P/D ratio determination. In fact, in a system wherein two pressure sensors are simultaneously placed in proper locations to take the proximal and distal readings, the readings are taken at substantially the same time.

Having described a number of exemplary applications of the host system 100 and its multipurpose, multimode architecture the breadth of potential configurations/applications of this architecture is demonstrated through two additional uses that involve the incorporation of a sensor orientation/ displacement signal and a temperature sensor signal received by the PCI card 112 of the host system 100. The host system 100, for example, receives pressure sensor signals and a sensor displacement signal enabling the host system 100 to render a map of pressure variations along a vessel. The resulting substantially real-time graphical display can be used, for example, to locate a stenosis or guide optimal placement of treatment of a vessel blockage. In yet another application supported by the host system 100, a position sensors identifying angular displacement as well as displacement along the length of a vessel are integrated, by the host system, with a temperature sensor mounted upon a flexible elongate member to provide a temperature map for the walls of a vessel to identify lesions. Such map is created by the host system 100 by rotating a temperature sensor placed against the vessel is wall and drawing the temperature sensor back along the vessel. The host system 100 receives and integrates the signals provided by the temperature and position sensors and renders a corresponding map.

Illustrative embodiments of the present invention and certain variations thereof have been provided in the Figures and accompanying written description. Those skilled in the art will readily appreciate from the above disclosure that many variations to the disclosed embodiment are possible in alternative embodiments of the invention. Such modifications include, by way of example, modifications to the form and/or content of the disclosed functions and functional blocks of the disclosed architecture, the measurements processed by the host system, the calculations arising from the measurements, the methods for setting modes and acquiring the measurements. Additionally, imaging data, such as Intravascular Ultrasound, Magnetic Resonance Imaging, Optical Coherence Tomography, etc., may be obtained, analyzed, and/or displayed upon the multipurpose application interface supported by the host system described hereinabove. The present invention is not intended to be limited to the disclosed embodiments. Rather the present invention is intended to cover the disclosed embodiments as well as others falling within the scope and spirit of the invention to the fullest extent permitted in view of this disclosure and the inventions defined by the claims appended herein below.

What is claimed is:

1. An intravascular sensing system, comprising:
a touch screen display; and
a computing device in communication with the touch screen display, wherein the computing device is operable to:
receive first intravascular data obtained by a first intravascular physiologic sensor coupled to a flexible elongate member positioned within a vessel of a patient, wherein the first intravascular data comprises intravascular physiological data;
display, with the touch screen display, a first display mode option and a second display mode option, the first display mode being different from the second display mode;
receive a first touch input from a user on the touch screen display, the first touch input selecting the first display mode option;
output, to the touch screen display, a first graphical representation of the first intravascular data in the first display mode;
receive a second touch input from the user on the touch screen display, the second touch input selecting an intravascular measurement associated with the first intravascular data and the first display mode option on the touch screen display; and
output, to the touch screen display based on the received second touch input from the user, a graphical representation of the selected intravascular measurement in the first display mode.

2. The intravascular sensing system of claim 1, further comprising a second intravascular physiologic sensor.

3. The intravascular sensing system of claim 2, wherein the computing device is further operable to:
receive second intravascular data obtained by the second intravascular physiologic sensor,
output, to the touch screen display, a second graphical representation of the second intravascular data.

4. The intravascular sensing system of claim 3, wherein the computing device is further operable to receive a third touch input from the user on the touch screen display, the third touch input selecting an intravascular measurement associated with either the first intravascular data or the second intravascular data; and
output, to the touch screen display based on the received third touch input from the user, a graphical representation of the selected intravascular measurement.

5. The intravascular sensing system of claim 3, wherein the computing device is further operable to receive a third touch input from the user on the touch screen display, the third touch input selecting an intravascular measurement associated with both the first intravascular data and the second intravascular data; and
output, to the touch screen display based on the received third touch input from the user, a graphical representation of the selected intravascular measurement.

6. The intravascular sensing system of claim 3, wherein the computing device is further operable to toggle between the first graphical representation and the second graphical representation in response to a user input.

7. The intravascular sensing system of claim 6, wherein the touch screen display includes a user input option to toggle between the first graphical representation and the second graphical representation.

8. The intravascular sensing system of claim 3, wherein the second intravascular data comprises at least one of intravascular pressure data or intravascular flow data.

9. The intravascular sensing system of claim 1, wherein the first intravascular data comprises at least one of intravascular pressure data or intravascular flow data.

10. The intravascular sensing system of claim 1, wherein the computing device is further operable to receive a third touch input from the user selecting the second display mode option on the touch screen display.

11. The intravascular sensing system of claim 1, wherein the touch screen display is configured to display the first graphical representation of the first intravascular data in the second display mode.

12. The intravascular sensing system of claim 1, wherein the first display mode and the second display mode are associated with different intravascular sensor types.

13. The intravascular sensing system of claim 1, wherein the computing device is further operable to:
receive second intravascular data obtained by an intravascular ultrasound (IVUS) sensor,
output, to the touch screen display, a second graphical representation of the second intravascular data.

* * * * *